United States Patent
Wipf et al.

(10) Patent No.: US 9,402,839 B2
(45) Date of Patent: *Aug. 2, 2016

(54) SELECTIVE TARGETING AGENTS FOR MITOCHONDRIA

(71) Applicant: University of Pittsburgh—Of the Commonwealth System of Higher Education, Pittsburgh, PA (US)

(72) Inventors: Peter Wipf, Pittsburgh, PA (US); Jingbo Xiao, Pittsburgh, PA (US); Mitchell P. Fink, Pittsburgh, PA (US); Valerian Kagan, Pittsburgh, PA (US); Yulia Tyurina, Pittsburgh, PA (US); Anthony J. Kanai, Pittsburgh, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/619,680

(22) Filed: Feb. 11, 2015

(65) Prior Publication Data

US 2015/0297578 A1    Oct. 22, 2015

Related U.S. Application Data

(63) Continuation of application No. 14/058,461, filed on Oct. 21, 2013, now Pat. No. 9,006,186, which is a continuation of application No. 12/750,891, filed on Mar. 31, 2010, now abandoned, which is a continuation of application No. 11/565,779, filed on Dec. 1, 2006, now Pat. No. 7,718,603, which is a continuation-in-part of application No. 11/465,524, filed on Aug. 18, 2006, now abandoned, which is a continuation-in-part of application No. 11/465,162, filed on Aug. 17, 2006, now Pat. No. 7,528,174.

(60) Provisional application No. 60/757,044, filed on Jan. 6, 2006.

(51) Int. Cl.
| | |
|---|---|
| *A61K 47/42* | (2006.01) |
| *A61K 31/4468* | (2006.01) |
| *C07K 7/06* | (2006.01) |
| *A61K 31/555* | (2006.01) |
| *A61K 31/7034* | (2006.01) |
| *A61K 31/7048* | (2006.01) |
| *A61K 47/48* | (2006.01) |
| *C07K 5/08* | (2006.01) |
| *C07K 5/10* | (2006.01) |

(52) U.S. Cl.
CPC ........... *A61K 31/4468* (2013.01); *A61K 31/555* (2013.01); *A61K 31/7034* (2013.01); *A61K 31/7048* (2013.01); *A61K 47/481* (2013.01); *A61K 47/48023* (2013.01); *A61K 47/48246* (2013.01); *C07K 5/08* (2013.01); *C07K 5/10* (2013.01); *C07K 7/06* (2013.01)

(58) Field of Classification Search
None
See application file for complete search history.

(56) References Cited

U.S. PATENT DOCUMENTS

| | | |
|---|---|---|
| 6,331,532 B1 | 12/2001 | Murphy et al. |
| 7,528,174 B2 | 5/2009 | Wipf et al. |
| 7,718,603 B1 | 5/2010 | Wipf et al. |
| 2005/0107366 A1 | 5/2005 | Carney et al. |
| 2005/0169904 A1 | 8/2005 | Payne |
| 2005/0245487 A1 | 11/2005 | Murphy et al. |
| 2007/0161544 A1 | 7/2007 | Wipf et al. |
| 2007/0161573 A1 | 7/2007 | Wipf et al. |
| 2009/0042808 A1 | 2/2009 | Fink et al. |
| 2010/0035869 A1 | 2/2010 | Wipf et al. |

FOREIGN PATENT DOCUMENTS

| | | |
|---|---|---|
| WO | 2010009389 A1 | 1/2010 |
| WO | 2010009405 A1 | 1/2010 |

OTHER PUBLICATIONS

Mota-Filipe et al. "A Membrane-Permeable Radical Scavenger Reduces the Organ Injury in Hemorrhagic Shock" Shock, vol. 12, No. 4, pp. 255-261, 1999.*

Kanai, A. et al., Mitochondrial Targeting of Radioprotectants Using Peptidyl Conjugates. Org Biomol Chem. Jan. 21, 2007; 5(2): 307-309.

Abashkin YG, Burt SK. (salen)MnIII compounds as nonpeptidyl mimics of catalase. Mechanism-based tuning of catalase activity: a theoretical study. Inorg Chem. Mar. 7, 2005;44(5):1425-32.

Baker RD, et al. Polarized Caco-2 cells. Effect of reactive oxygen metabolites on enterocyte barrier function. Dig Dis Sci. Mar. 1995; 40(3):510-8.

(Continued)

*Primary Examiner* — Christina Bradley
(74) *Attorney, Agent, or Firm* — The Webb Law Firm

(57) ABSTRACT

The present invention provides a composition and related methods for delivering cargo to a mitochondria which includes (a) a membrane active peptidyl fragment having a high affinity with the mitochondria and (b) cargo. The cargo may be selected from a wide variety of desired cargos which are to be delivered to the mitochondria for a specific purpose. Compositions and methods are disclosed for treating an illness that is caused or associated with cellular damage or dysfunction which is caused by excessive mitochondrial production of reaction oxygen species (ROS). Compositions which act as mitochondria-selective targeting agents using the structural signaling of the β-turn recognizable by cells as mitochondria) targeting sequences are discussed. Mitochondria and cell death by way of apoptosis is inhibited as a result of the ROS-scavenging activity, thereby increasing the survival rate of the patient.

16 Claims, 12 Drawing Sheets

(56) References Cited

OTHER PUBLICATIONS

Banan A, et al. Activation of delta-isoform of protein kinase C is required for oxidant-induced disruption of both the microtubule cytoskeleton and permeability barrier of intestinal epithelia. J Pharmacol Exp Ther. Oct. 2002;303(1):17-28.
Batinic-Haberle I, et al. New PEG-ylated Mn(III) porphyrins approaching catalytic activity of SOD enzyme. Dalton Trans. Jan. 28, 2006;(4):617-24.
Bottcher CFJ, et al. A rapid and sensitive sub-micro phosphorous determination. Anal Chim Acta. 1961 24, 203-204.
Butler MS, Buss AD. Natural products—the future scaffolds for novel antibiotics? Biochem Pharmacol. Mar. 30, 2006;71(7):919-29.
Cairns CB. Rude unhinging of the machinery of life: metabolic approaches to hemorrhagic shock. Curr Opin Crit Care. Dec. 2001;7(6):437-43.
Clement AM et al. Wild-type nonneuronal cells extend survival of SOD1 mutant motor neurons in ALS mice. Science. Oct. 3, 2003;302(5642):113-7.
Cuzzocrea et al., Effects of tempol, a membrane-permeable radical scavenger, in a gerbil model of brain injury. Brain Research, 2000, 875, 96-106.
Dolder M, et al. Mitochondrial creatine kinase in contact sites: interaction with porin and adenine nucleotide translocase, role in permeability transition and sensitivity to oxidative damage. Biol Signals Recept. Jan.-Apr. 2001;10(1-2):93-111.
Edmonds MK, Abell AD. Design and synthesis of a conformationally restricted trans peptide isostere based on the bioactive conformations of the sasquinavir and nelfinavir. J Org Chem. Jun. 1, 2001;66(11):3747-52.
Epperly MW, et al. Manganese superoxide dismutase (SOD2) inhibits radiation induced apoptosis by stabilization of the mitochondrial membrane. Rad Res 2002; 157: 568-577.
Folch J, et al. A simple method for the isolation and purification of total lipids from animal tissues. J. Biol. Chem. 1957 226: 497-509.
Gibson SE, Lecci C. Amino acid derived macrocycles—an area driven by synthesis or application? Angew Chem Int Ed Engl. Feb. 20, 2006;45(9):1364-77.
Hahn et al., Tempol, a Stable Free Radical, Is a Novel Murine Radiation Protector. Cancer Research, 1992, 52, 1750-1753.
Hahn SM, et al. Mn(III)-Desferrioxamine superoxide dismutase-mimic: alternative modes of action. Arch. Biochem. Biophy. Jul. 1991;288(1):215-219.
Han X, et al. Proinflammatory cytokines cause NO-dependent and-independent changes in expression and localization of tight junction proteins in intestinal epithelial cells. Shock. Mar. 2003;19(3):229-37.
He H. Mannopeptimycins, a novel class of glycopeptide antibiotics active against gram-positive bacteria. Appl Microbiol. Biotechnol. Jun. 2005;67(4):444-52.
Imai H, et al. Protection from inactivation of the adenine nucleotide translocator during hypoglycaemia-induced apoptosis by mitochondrial. Biochem J. May 1, 2003;371(Pt 3):799-809.
Itami C, et al. Superoxide dismutase mimetic activities of metal complexes of L-2(2-pyridyl)-1-pyrroline-5-carboxylic acid (pyrimine). Biochem Biophys Res Commun. Dec. 15, 1993;197(2):536-41.
Iverson SL, Orrenius S. The cardiolipin-cytochrome c interaction and the mitochondrial regulation of apoptosis. Arch Biochem Biophys. Mar. 1, 2004;423(1):37-46.
Jackel et al. (Fluorine in Peptide Design and Protein Engineering. Eur. J. Org. Chem., 2005, 4483-4503, published online Sep. 23, 2005).
Kagan VE, et al. A role for oxidative stress in apoptosis: oxidation and externalization of phosphatidylserine is required for macrophage clearance of cells undergoing Fas-medicated apoptosis. J Immunol. Jul. 1, 2002;169(1):487-99.
Kagan VE, et al. Cytochrome c acts as a cardiolipin oxygenase required for release of proapoptotic factors. Nat Chem Biol. Sep. 2005;1(4):223-32.

Kagan VE, et al. Oxidative lipidomics of apoptosis: redox catalytic interactions of cytochrome c with cardiolipin and phosphatidylserine. Free Radic Biol Med. Dec. 15, 2004;37(12):1963-85.
Kanai AJ, et al. Manganese superoxide dismutase gene therapy protects against irradiation-induced cystitis. Am J Physiol Renal Physiol. Dec. 2002;283(6):F1304-12.
Kanai A, et al. Differing roles of mitochondrial nitric oxide synthase in cardiomyocytes and urothelial cells. Am J Physiol Heart Circ Physiol. Jan. 2004;286(1):H13-21.
Kanai AJ, et al. Identification of a neuronal nitric oxide synthase in isolated cardiac mitochondria using electrochemical detection. Proc Natl Acad Sci U S A. Nov. 20, 2001;98(24):14126-31.
Kanai A, Peterson J. Function and regulation of mitochondrially produced nitric oxide in cardiomyocytes. Am J Physiol Heart Circ Physiol. Jan. 2004;286(1):H11-2.
Kelso GF, et al P. Selective targeting of a redox-active ubiquinone to mitochondria within cells: antioxidant and antiapoptotic properties. J Biol Chem. Feb. 16, 2001;276(7):4588-96.
Kentner R, et al. Early antioxidant therapy with Tempol during hemorrhagic shock increases survival in rats. J Trauma. Nov. 2002;53(5):968-77.
Konorev EA, et al. Cell-permeable superoxide dismutase and glutathione peroxidase mimetics afford superior protection against doxorubicin-induced cardiotoxicity: the role of reactive oxygen and nitrogen intermediates. Arch Biochem Biophys. Aug. 15, 1999;368(2):421-8.
Lacza et al. ("Mitochondrial NO and reactive nitrogen species production: Does mtNOS exist?" Nitric Oxide, 2006, 14, 162-8, especially p. 162-3).
Lee DL, Hodges RS. Structure-activity relationships of de novo designed cyclic antimicrobial peptides based on gramicidin S. Biopolymers. 2003;71(1):28-48.
Liaw et al., Effects Of A Membrane-Permeable Radical Scavenger, Tempol, On Intraperitoneal Sepsis-Induced Organ Injury in Rats. Shock, 2005, 23, 88-96.
Macias CA, et al. Treatment with a novel hemigramicidin-TEMPO conjugate prolongs survival in a rat model of lethal hemorrhagic shock. Ann Surg. Feb. 2007;245(2):305-14.
McDonald et al., Tempol reduces infarct size in rodent models of regional myocardial ischemia and reperfusion. Free Radical Biology and Medicine, 1999, 27, 493-503.
Nakane et al. ("Novel Potent and Selective Inhibitors of Inducible Nitric Oxide Synthase." Mol. Pharm., 1995, 47, 831-4).
Niccolai et al., "An investigation of the mechanisms of nitroxide-induced proton relaxation enhancements in biopolymers." J. Phys. Chem., 1994, 88, 5689-5692.
Nicolas P, et al. Molecular strategies in biological evolution of antimicrobial peptides. Peptides. Nov. 2003;24(11):1669-80.
Nishiyama et al., Systemic and Regional Hemodynamic Responses to Tempol in Angiotensin II-Infused Hypertensive Rats. Hypertension, 2001, 37, 77-83.
Olcott AP, et al. A salen-manganese catalytic free radical scavenger inhibits type 1 diabetes and islet allograft rejection. Diabetes. Oct. 2004;53(10):2574-80.
Payne JW, et al. Conformer profiles and biological activities of peptides. Curr Org Chem. 2002, 6: 1221-46.
Pieper GM, et al. Protective mechanisms of a metalloporphyrinic peroxynitrite decomposition catalyst, WW85, in rat cardiac transplants. J Pharmacol Exp Ther. Jul. 2005;314(1):53-60.
Porter EA, et al. Mimicry of host-defense peptides by unnatural oligomers: antimicrobial beta-peptides. J Am Chem Soc. Jun. 26, 2002;124(25):7324-30.
Raguse TL, et al. Structure-activity studies of 14-helical antimicrobial beta-peptides: probing the relationship between conformational stability and antimicrobial potency. J Am Chem Soc. Oct. 30, 2002;124(43):12774-85.
Schnackenberg & Wilcox, Two-Week Administration of Tempol Attenuates Both Hypertension and Renal Excretion of 8-Iso Prostaglandin F2. Hypertension, 1999, 33, 424-428.
Shidoji Y, et al. Loss of molecular interaction between cytochrome c and cardiolipin due to lipid peroxidation. Biochem Biophys Res Commun. Oct 22, 1999;264(2):343-7.

(56) References Cited

OTHER PUBLICATIONS

Tamaki M, et al. CD spectra and cyclization of linear pentapeptides as gramicidin S precursors with a benzyloxycarbonyl group on the side chain of Orn residue. Bull Chem Soc Jpn. 1993 66(10): 3113-15.

Thiemermann, Membrane-permeable radical scavengers (tempol) for shock, ischemia-reperfusion injury and inflammation. Crit. Care Med., 2003, 31, S76-S84.

Tuominen EK, et al. Phospholipid-cytochrome c interaction: evidence for the extended lipid anchorage. J Biol Chem. Mar. 15, 2002;277(11):8822-6.

Wade D, et al. Antibiotic properties of novel synthetic temporin A analogs and a cecropin A-temporin A hybrid peptid. Protein Pept Lett. Dec. 2002;9(6):533-43.

Wattanasirichaigoon S, et al. Effect of mesenteric ischemia and reperfusion or hemorrhagic shock on intestinal mucosal permeability and ATP content in rats. Shock. Aug. 1999;12(2):127-33.

Wipf P, Xiao J. Convergent approach to (E)-alkene and cyclopropane peptide isosteres. Org Lett. Jan. 6, 2005;7(1):103-6.

Wipf P, et al. Mitochondrial targeting of selective electron scavengers: synthesis and biological analysis of hemigramicidin-TEMPO conjugates. J Am Chem Soc. Sep. 14, 2005;127(36):12460-1.

Wipf P, et al. Methyl and (Trifluoromethyl)alkene peptide isosteres: synthesis and evaluation of their potential as beta-turn promoters and peptide mimetics. J Org Chem. Sep. 4, 1998;63(18):6088-6089.

Wipf P, et al. Synthesis of chemoreversible prodrugs of ara-C with variable time-release profiles. Biological evaluation of their apoptotic activity. Bioorg Med Chem. Oct. 1996;4(10):1585-96.

Wipf P, et al. Imine Additions of Internal Alkynes for the Synthesis of Trisubstituted (E)-Alkene and Cyclopropane Peptide Isosteres. Adv. Synth. Cat. Oct. 2005;347(11-13):1605-13.

Wood PL, et al. Neurotoxicity of reactive aldehydes: the concept of "aldehyde load" as demonstrated by neuroprotection with hydroxylamines. Brain Res. Jun. 20, 2006;1095(1):190-9.

Xiao J, et al. Electrostatic versus steric effects in peptidomimicry: synthesis and secondary structure analysis of gramicidin S analogues with (E)-alkene peptide isosteres. J Am Chem Soc. Apr. 27, 2005;127(16):5742-3.

Yamamoto S, et al R. Anti-tumor promoting action of phthalic acid mono-n-butyl ester cupric salt, a biomimetic superoxide dismutase. Carcinogenesis. May 1990;11(5):749-54.

Yang R, et al. Ethyl pyruvate modulates inflammatory gene expression in mice subjected to hemorrhagic shock. Am J Physiol Gastrointest Liver Physiol. Jul. 2002;283(1):G212-22.

Zhao et al. "Cell-permeable peptide antioxidants targeted to inner mitochondrial membrane inhibit mitochondrial swelling, oxidative cell death, and reperfusion injury." J. Biol. Chem., 2004, 279, 34682-90.

\* cited by examiner

SELECTIVE TARGETING AGENTS FOR MITOCHONDRIA

CROSS-REFERENCE TO RELATED APPLICATIONS

This application is a continuation of U.S. patent application Ser. No. 14/058,461, filed Oct. 21, 2013, now U.S. Pat. No. 9,006,186, issued Apr. 14, 2015, which is a continuation of U.S. patent application Ser. No. 12/750,891, filed Mar. 31, 2010, now abandoned, which is a continuation of U.S. patent application Ser. No. 11/565,779, filed Dec. 1, 2006, now U.S. Pat. No. 7,718,603, issued May 18, 2010, which is a continuation-in-part of U.S. patent application Ser. No. 11/465,524, filed Aug. 18, 2006, now abandoned, which was a continuation-in-part of U.S. patent application Ser. No. 11/465,162, filed Aug. 17, 2006, now U.S. Pat. No. 7,528,174, issued May 5, 2009, which in turn claimed the benefit of U.S. Provisional Application No. 60/757,044 entitled "Selective Targeting Agents for Mitochondria" filed on Jan. 6, 2006, each of which is incorporated herein by reference in its entirety.

GOVERNMENT SUPPORT

This invention was made with Government support under Grant No. W81XWH-05-2-0026, awarded by DARPA, and Grant No. GM067082, awarded by the National Institutes of Health. The government has certain rights in the invention.

BACKGROUND OF THE INVENTION

1. Field of the Invention

The present invention relates to compositions and methods for providing mitochondria-selective targeting agents bonded or linked to desired cargo, such as radical scavenging agents. In another embodiment, the cargo transported by mitochondrial-selective targeting agents may include an inhibitor of nitric oxide synthase ("NOS") enzyme activity. Some embodiments employ membrane active peptidyl fragments having a high affinity with the mitochondria and the cargo. Some embodiments focus on compositions and methods of TEMPO conjugates, particularly synthetic Gramicidin S-peptidyl TEMPO (2,2,6,6-tetramethylpiperidine-N-oxyl) conjugates.

2. Description of the Prior Art

Cells typically undergo some degree of oxidative stress by way of generating reactive oxygen species ("ROS") and reactive nitrogen species ("RNS"). Specifically, the cellular respiration pathway generates ROS and RNS within the mitochondrial membrane of the cell, see Kelso et al., *Selective Targeting of a Redox-active Ubiquinone to Mitochondria within Cells: Antioxidant and Antiapoptotic Properties*, J. BIOL. CHEM. 276:4588 (2001). Reactive oxygen species include free radicals, reactive anions containing oxygen atoms, and molecules containing oxygen atoms that can either produce free radicals or are chemically activated by them. Specific examples include superoxide anion, hydroxyl radical, and hydroperoxides.

Naturally occurring enzymes, such as superoxide dismutase ("SOD") and catalase salvage ROS and RNS radicals to allow normal metabolic activity to occur.

Significant deviations from cell homeostasis, such as hemorrhagic shock, lead to an oxidative stress state, thereby causing "electron leakage" from the mitochondrial membrane. Said "electron leakage" produces an excess amount of ROS for which the cell's natural antioxidants cannot compensate. Specifically, SOD cannot accommodate the excess production of ROS associated with hemorrhagic shock which ultimately leads to premature mitochondria dysfunction and cell death via apoptosis, see Kentner et al., *Early Antioxidant Therapy with TEMPOL during Hemorrhagic Shock Increases Survival in Rats*, J. OF TRAUMA® INJURY, INFECTION, AND CRITICAL CARE, 968 (2002).

Cardiolipin ("CL") is an anionic phospholipid exclusively found in the inner mitochondrial membrane of eukaryotic cells, see Iverson, S. L. and S. Orrenius, *The cardiolipin-cytochrome c interaction and the mitochondria) regulation of apoptosis*, ARCH. BIOCHEM. 423:37-46 (2003).

Under normal conditions, the pro-apoptotic protein cytochrome c is anchored to the mitochondrial inner membrane by binding with CL, see Tuominen, E. K. J., et al. *Phospholipid cytochrome c interaction: evidence for the extended lipid anchorage*, J. BIOL. CHEM., 277:8822-8826 (2002). The acyl moieties of CL are susceptible to peroxidation by reactive oxygen species. When ROS are generated within mitochondria in excess quantities, cytochrome C bound to CL can function as an oxidase and induces extensive peroxidation of CL in the mitochondrial membrane, see Kagan, V. E. et al., *Cytochrome c acts as a cardiolipin oxygenase required, for release of proapoptotic, factors*, NATURE CHEM. BIOL. 1:223-232 (2005); also Kagan, V. E. et al., *Oxidative lipidomics of apoptosis: redox catalytic interactions of cytochrome c with cardiolipin and phosphatidylserine*, FREE RAH. BIOL. MED. 37:1963-1985 (2005).

The peroxidation of the CL weakens the binding between the CL and cytochrome C, see Shidoji, Y. et al., *Loss of molecular interaction between cytochrome C and cardiolipin due to lipid peroxidation*, BIOCHEM. BIOPHYS. RES. COMM. 264:343-347 (1999). This leads to the release of the cytochrome C into the mitochondrial intermembrane space, inducing apoptotic cell death.

Further, the peroxidation of CL has the effect of opening the mitochondrial permeability transition pore ("MPTP"), see Dolder, M. et al., *Mitochondria creatine kinase in contact sites: Interaction with porin and adenine nucleotide translocase, role in permeability transition and sensitivity to oxidative damage*, BIOL. SIGNALS RECEPT., 10:93-111 (2001); also Imai, H. et al., *Protection from inactivation of the adenine nucleotide translocator during hypoglycaemia-induced apoptosis by mitochondria/phospholipid hydroperoxide glutathione peroxidase*, BIOCHEM. J., 371:799-809 (2003). Accordingly, the mitochondrial membrane swells and releases the cytochrome C into the cytosol. Excess cytochrome C in the cytosol leads to cellular apoptosis, see Iverson, S. L. et al. *The cardiolipin-cytochrome c interaction and the mitochondria regulation of apoptosis*, ARCH. BIOCHEM. BIOPHYS. 423:37-46 (2003).

Moreover, mitochondrial dysfunction and cell death may ultimately lead to multiple organ failure despite resuscitative efforts or supplemental oxygen supply, see Cairns, C., *Rude Unhinging of the Machinery of Life: Metabolic approaches to hemorrhagic Shock*, CURRENT CRITICAL CARE, 7:437 (2001). Accordingly, there is a need in the art for an antioxidant mimic similar to SOD which scavenges the ROS, thereby reducing oxidative stress. Reduction of oxidative stress delays, even inhibits, physiological conditions that otherwise might occur, such as hypoxia.

Also, there is also a need to improve the permeability of antioxidants' penetration of the cellular membrane. One of the limitations of SOD is that it cannot easily penetrate the cell membrane. However, nitroxide radicals, such as TEMPO (2,2,6,6-tetramethylpiperidine-N-oxyl) and its derivatives, have been shown to penetrate the cell membrane better than SOD. Further, nitroxide radicals like TEMPO prevent the formation of ROS, particularly superoxide, due to their reduction by the mitochondrial electron transport chain to hydroxyl amine radical scavengers, see Wipf P. et al., *Mitochondria targeting of selective electron scavengers: synthesis and biological analysis of hemigramicidin-TEMPO conjugates*, J. AM. CHEM. SOC. 127:12460-12461. Accordingly, selective delivery of TEMPO derivatives may lead to a therapeutically beneficial reduction of ROS and may delay or inhibit cell death due to the reduction of oxidative stress on the cell.

This selective delivery may be accomplished by way of a number of different pathways—i.e., a biological or chemical moiety has a specific targeting sequence for penetration of the cell membrane, ultimately being taken up by the mitochondrial membrane. Selective delivery of a nitroxide SOD mimic into the mitochondrial membrane has proven difficult. Accordingly, there is a need in the art for effective and selective delivery of TEMPO antioxidant derivatives that specifically target the mitochondrial membrane to help reduce the ROS and RNS species. Said antioxidants also help prevent cellular and mitochondria apoptotic activity which often results due to increased ROS species, see Kelso et al., *Selective Targeting of a Redox-active Ubiquinone to Mitochondria within Cells: Antioxidant and Antiapoptotic Properties*, J. BIOL. CHEM., 276: 4588 (2001).

U.S. Patent Application 2005/0169904 discloses a conjugate which comprises the following: (i) a mitochondrial membrane-permeant peptide; (ii) a mitochondrial-active agent or compound of interest such as a detectable group or compound, an active mitochondrial protein or peptide, nucleic acids, drug or signaling agent; and, (iii) a mitochondrial targeting sequence linking said mitochondrial membrane-permeant peptide and said active mitochondrial protein or peptide. The targeting sequence of the conjugate is cleaved within the mitochondrial matrix, not within the cellular cytoplasm of a target cell into which said mitochondrial-active agent or compound is to be delivered. Methods of use of these compounds and agents are also disclosed within the publication. A disadvantage of this metholodology is that it requires cleavage of the peptide sequence in order to release the active agent.

U.S. Pat. No. 6,331,532 and U.S. Patent Application 2005/0245487 A1 disclose mitochondrially targeted antioxidant compounds. The compound comprises a lipophilic cation covalently bonded to an antioxidant moiety. Pharmaceutical compositions containing the mitochondrially targeted antioxidant compounds, and methods of therapy or prophylaxis of patients who would benefit from reduced oxidative stress are disclosed. This methodology relies on ionic or lipophilic interactions and is less selective than the present invention.

U.S. Patent Application 2005/0107366 A1 discloses a pharmaceutical composition that is covalently bound to a non-toxic spin trapping compound. Spin trapping compositions generally have been known to be effective in treating a variety of disorders. Spin trapping compounds are molecules that have an unpaired electron (i.e., paramagnetic), form a stable compound or complex with a free radical, and lack cytotoxicity. One example of a spin trapping compound is TEMPO. These spin trapping compounds, such as TEMPO, provide a unique signal that can be measured by electron spin spectroscopy ("ESR"). Since an effective mitochondrial-targeting sequence is not used, this approach is not as efficient as the present invention.

TEMPO and its derivatives are antioxidants that have been shown to improve physiologic variables after induced hemorrhagic shock, such as heart rate, systolic blood pressure, acid-base balance, serum antioxidant status, and survival time, see Kentner et al., *Early Antioxidant Therapy with TEM-POL during Hemorrhagic Shock Increases Survival in Rats*, J. OF TRAUMA® INJURY, INFECTION, AND CRITICAL CARE, 968 (2002). In general, effective levels of administered TEMPO are too high to accomplish therapeutic effects.

Therefore, in spite of the foregoing prior art, there remains a very real need for a composition and associated methods for delivering cargo of various types to mitochondria. In one embodiment, a composition comprising membrane active peptidyl fragments having a high affinity with the mitochondria linked to cargo is provided. The cargo may be selected from a large group of candidates. The invention also contemplates compositions and methods for effectively treating a condition that is caused by excessive mitochondria production of ROS and RNS in the mitochondrial membrane.

SUMMARY OF THE INVENTION

The present invention has met the hereinbefore described need by providing compositions and methods as disclosed for treating a condition, including a disease or other medical condition, which is caused by excessive mitochondrial production of ROS in the mitochondrial membrane.

In its broader aspects, the invention contemplates a composition for delivering cargo to a mitochondria comprising (a) a membrane active peptidyl fragment having a high affinity with the mitochondria and (b) a cargo. The composition may have a property selected from the group consisting of antioxidant, radioprotective, protective, anti-apoptotic, therapeutic, ameliorative, NOS antagonist and combinations thereof. The composition may be selected from the group consisting of XJB-5-234, XJB-5-133, XJB-5-241, and XJB-5-127. Other compositions as herein described may be employed.

The membrane active peptidyl fragment may have a $\beta$-turn motif.

In one embodiment, the membrane active peptidyl fragment may be from an antibiotic molecule that acts by targeting the bacterial cell wall. A wide variety of cargos may be selected for use in the composition and method of the invention. One category of cargo employable in the invention is a radical scavenging agent. Another category of cargo is an NOS antagonist.

In a further embodiment of the invention, a patient is treated by administering to the patient a composition, and effecting by said administration inhibiting patient cells from injury. The composition has (a) a membrane active peptidyl fragment having a high affinity with mitochondria and (b) cargo.

In a preferred embodiment, the compositions are conjugates of Gramicidin S peptidyl fragments and TEMPO derivatives. The Gramicidin S peptidyl fragment is either Gramicidin S or a hemigramicidin fragment. In a further embodiment, a hemigramicidin (i.e., a fragmented version of Gramicidin S with additional functional groups) motif with an amide bond isostere constitute the Gramicidin moiety of the TEMPO-peptidyl conjugate. In a preferred embodiment, the amide bond isostere is an (E)-alkene moiety.

In yet another embodiment, the mitochondrial targeting agent is a GS peptidyl fragment which comprises peptide bond mimetics.

Yet another embodiment provides a method for delivering antioxidants, such as TEMPO, for example, into cells to mitochondria. Specifically, the peptidyl conjugates comprise a targeting sequence which is recognizable by the mitochondria and also permeable to the mitochondria membrane. The peptidyl conjugate thereby "anchors" the antioxidant "payload" into the mitochondrial membrane whereby the antioxidant acts as an electron scavenger of the ROS present within the membrane. Accordingly, the electron scavenging activity of the antioxidant helps resist mitochondrial dysfunction and cell death.

Another preferred embodiment provides a method for therapeutically administering the TEMPO-peptidyl conjugate to patients with hemorrhagic shock to help prolong survival until it is feasible to obtain control of the bleeding vessels of the patient. Another related embodiment provides a method for therapeutically administering the TEMPO-peptidyl conjugate to patients with hemorrhagic shock to help prolong survival until it is feasible to obtain control of the bleeding vessels of the patient, in spite of a lack of resuscitation with blood or other non-sanguineous fluids. Yet another related embodiment provides a method for therapeutically administering the TEMPO-peptidyl conjugate to patients with hemorrhagic shock to help prolong survival until it is feasible to obtain control of the bleeding vessels of the patient, in spite of hypotension.

The invention also contemplates a composition for scavenging the radicals in a mitochondrial membrane comprising a radical scavenging agent and a membrane active compound having a high affinity with the mitochondria. It also contemplates a related method for delivering a composition to mitochondria comprising transporting to said mitochondrial membrane (a) a radical scavenging agent and (b) a membrane active compound having a high affinity with the mitochondrial membrane.

In another embodiment, the cargo which is covalently linked to the mitochondrial-selective targeting agents may be an inhibitor of nitric oxide synthase ("NOS") enzyme activity.

An object of this invention is to provide compositions which effectively act as mitochondria-selective targeting agents to help deliver an attached moiety to the mitochondria membrane.

Another object of this invention is to provide compositions transported by mitochondrial-selective targeting agents which may include an inhibitor of NOS enzyme activity Another object of this invention is to provide a method for delivering these agents effectively into cells and mitochondria where they act as electron scavengers.

Yet another object of the invention is to provide a method which provides agents that provide protection against mitochondrial dysfunction and cell apoptosis.

Yet another object of this invention is to prolong the survival of a patient that has suffered hemorrhagic shock.

A related object of this invention is to prolong the survival of a patient that has suffered hemorrhagic shock and has not been resuscitated with blood or non-sanguineous fluids.

Yet another related object of this invention is to prolong the survival of a patient that has suffered hemorrhagic shock and is hypotensive.

Still another object of the invention is to provide a composition and method for treating a condition, including a disease or other medical condition, which is the result of excessive mitochondrial production of ROS.

Yet another object of this invention is to provide a method for administering the composition to patients with a condition, including a disease or an illness, which is the result from excessive mitochondrial production of ROS.

These and other objects of the invention will be more fully understood from the following detailed description of the invention on reference to the illustrations and table appended hereto.

BRIEF DESCRIPTION OF THE DRAWINGS

FIG. 4A, panel A shows an FD4 read-out of TEMPOL which is used as a "positive control" for the gut mucosal protection assay. FIG. 4A, panel B shows an FD4 read-out of TEMPO conjugate XJB-5-208 reflecting gut mucosal protection. FIG. 4B, panel C shows an FD4 read-out of XJB-5-125 which has the TEMPO payload, but fails to provide protection against gut barrier dysfunction induced by hemorrhage. FIG. 4B, panel D shows an FD4 read-out of XJB-5-127 which lacks the TEMPO payload and fails to provide protection against gut barrier dysfunction induced by hemorrhage. FIG. 4C, panel E shows an FD4 read-out of TEMPO conjugate XJB-5-131 reflecting gut mucosal protection. FIG. 4C, panel F shows an FD4 read-out of XJB-5-133 which lacks the TEMPO payload even though it possesses the same hemigramicidin mitochondria targeting moiety as the most active compound, XJB-5-131. FIG. 4D, panel G shows an FD4 read-out of XJB-5-197 which has the TEMPO payload, but fails to provide protection against gut barrier dysfunction induced by hemorrhage. FIG. 4D, panel H shows an FD4 read-out of XJB-5-194 which lacks the TEMPO payload and fails to provide protection against gut barrier dysfunction induced by hemorrhage.

FIG. 9B is a graphical representation of the effects of intravenous treatment with XJB-5-131 on survival probability of rates subjected to volume controlled hemorrhagic shock.

DESCRIPTION OF THE PREFERRED EMBODIMENTS

Figure 1:
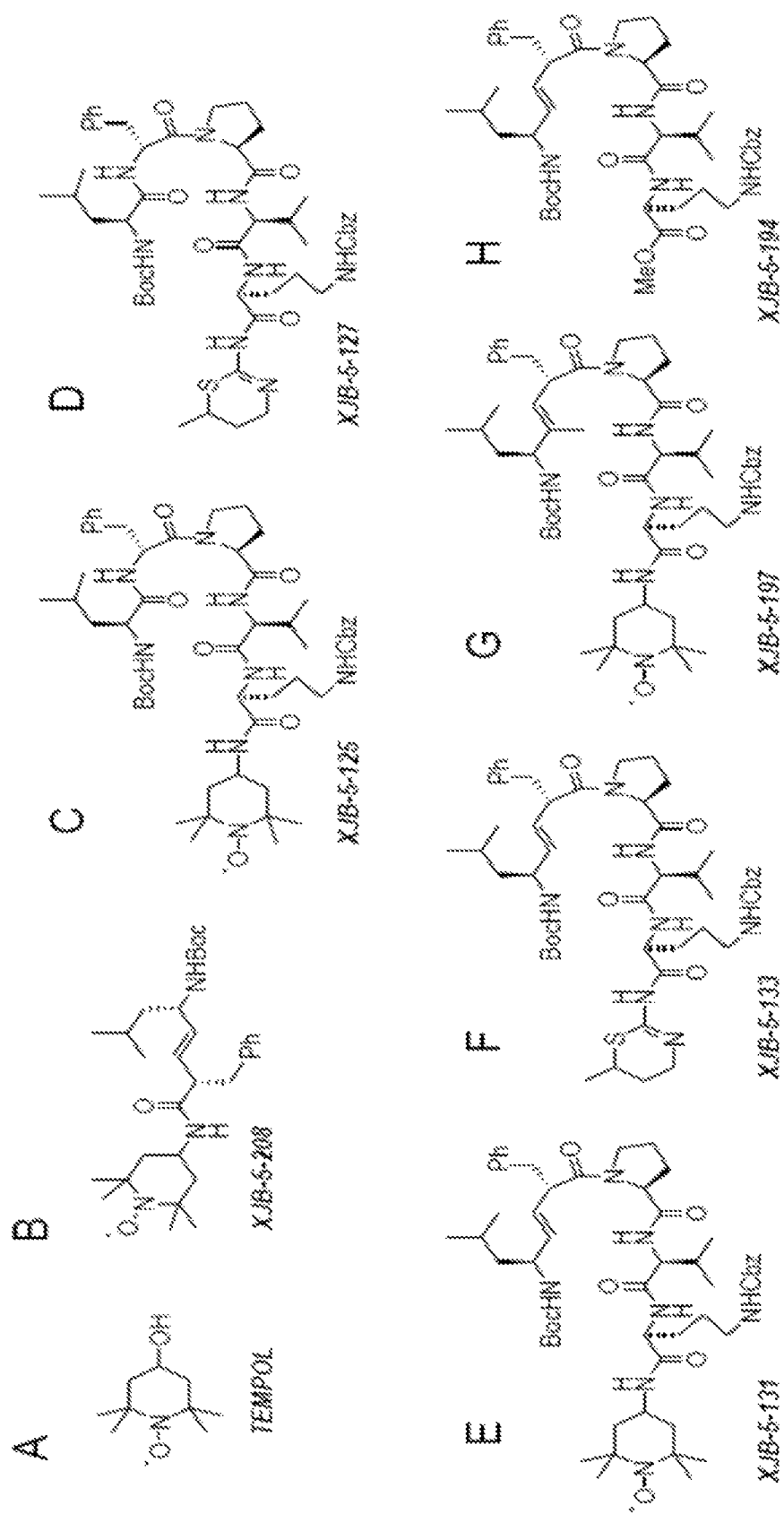
FIG. 1 depicts the chemical structure of TEMPOL and the seven hemigramicidin derivative compounds. Panel A shows TEMPOL. Panel B shows a dipeptidic TEMPO analog—XJB-5-208. Panel C shows a hemigramicidin-TEMPO conjugate—XJB-5-125. Panel D shows a hemigramicidin conjugate that has AMT functional moiety in place of the TEMPO moiety—XJB-5-127. Panel E shows a hemigramicidin-TEMPO conjugate—XJB-5-131. Panel F shows a hemigramicidin conjugate that has the AMT functional moiety in place of the TEMPO moiety—XJB-5-133. Panel G shows a hemigramicidin-TEMPO conjugate—XJB-5-197. Panel H shows a hemigramicidin compound that does not have the TEMPO or AMT moieties—XJB-5-194.

As used herein, the term "patient" refers to members of the animal kingdom including but not limited to human beings.

As used herein, the term "reactive oxygen species" ("ROS") includes, but is not limited to, superoxide anion, hydroxyl, and hydroperoxide radicals.

The present invention relates to compositions and methods for providing mitochondria-selective targeting agents bonded, as by covalent linking, for example, to desired cargo such as radical scavenging agents, for example.

In another embodiment, the cargo transported by mitochondria-selective targeting agents may include an inhibitor of NOS activity.

While the generation of ROS in small amounts is a typical byproduct of the cellular respiration pathway, certain conditions, including a disease or other medical condition, may occur in the patient when the amount of ROS is excessive to the point where natural enzyme mechanisms cannot scavenge the amount of ROS being produced.

The present invention provides compositions and methods that scavenge reactive oxygen species that are present within the mitochondrial membrane of the cell. These compositions and methods have the utility of being able to scavenge an excess amount of ROS being produced that naturally occurring enzymes SOD and catalase, among others, cannot cope with.

In a preferred embodiment of the invention, a composition for delivering cargo to a mitochondria comprises (a) a membrane active peptidyl fragment having a high affinity with mitochondria and (b) cargo. A related method which employs the delivery to mitochondria by means of a membrane active peptidyl fragment having a high affinity with the mitochondria is also contemplated.

The cargo may have a property selected from the group consisting of antioxidant, radioprotective, protective, anti-apoptotic, therapeutic, ameliorative, NOS antagonist and combinations thereof. The cargo may be selected from the group consisting of XJB-5-234, XJB-5-133, XJB-5-241, and XJB-5-127. It is preferred that the membrane active peptidyl have a β-turn motif and that the active peptidyl fragment is bonded to the cargo.

In one embodiment, the membrane active peptidyl fragment may be derived from an antibiotic. The fragment may be from an antibiotic molecule that acts by targeting the bacterial cell wall. The antibiotic is preferably selected from the group consisting of bacitracins, gramicidins, valinomycins, enniatins, alamethicins, beauvericin, serratomolide, sporidesmolide, tyrocidins, polymyxins, monamycins, and lissoclinum peptides.

The cargo may be categorized by the property of creating biological effects which endow the mitochondria with resistance to oxidative damage induced by free radicals. The cargo may be a radical scavenging agent. In one embodiment, the cargo may be selected from the group consisting of TEMPO and TEMPO moieties.

In another embodiment, the cargo may be categorized by the property of endowing the mitochondria with resistance to nitrosative damage.

In another embodiment, the cargo may be categorized by the property of inhibiting nitric oxide synthase enzyme activity. It will be appreciated that a wide variety of cargoes may be employed in the composition and with the method of the invention. Among the additionally preferred cargos are a cargo selected from the group consisting of a 2-amino-6-methyl-thiazine, a ubiquinone analog, a ubiquinone analog fragment moiety, a ubiquinone analog fragment moiety lacking a hydrophilic tail, a superoxide dismutase mimetic, a superoxide dismutase biomimetic and a salen-manganese compound.

In a therapeutic embodiment of the invention, a patient may be treated by administering to the patient a composition which inhibits patient cells injury. The cargo employed in this therapeutic method may serve to scavenge free radicals. In another embodiment of the method, the cargo may serve to inhibit nitric oxide synthase.

In one aspect of the invention, compounds possessing electron scavenger properties similar to SOD and catalase are disclosed. In another aspect of the invention, methods for targeting the mitochondria of the cell are discussed.

In one embodiment of the present invention, the compositions were derived from a covalent form of 4-amino-TEMPO and peptidyl fragments of Gramicidin S. As is known to one ordinarily skilled in the art, Gramicidin S is a well-known antibiotic and has a high affinity to bacterial membranes. Further, bacteria and mitochondria are structurally quite similar. Accordingly, it was found that appropriately folded peptidyl fragments of Gramicidin S, such as those having a β-turn, have a high affinity for mitochondria and are introduced into the mitochondria membrane and permeate through the cytoplasm membrane of the cell. Therefore, targeting of mitochondria by way of Gramicidin S peptidyl fragments proved to be useful. In another embodiment, the compositions were derived from a conjugate form of TEMPOL and peptidyl fragments of Gramicidin S.

Accordingly, using the Gramicidin S peptidyl fragments and alkene isosteres (beta turns) as "anchors," the TEMPO "payload" could be guided into the mitochondrial membrane.

In one embodiment, the Leu-$^D$Phe-Pro-Val-Orn fragment of hemigramicidin may advantageously be used as a targeting sequence. The β-turn motif of the Gramicidin-S fragment directs most of the polar functionality of the peptide strand into the core; the amino functional groups of Leu and Orn are acylated so that cytotoxicity of Gramicidin S is reduced.

Alkene isosteres such as (E)-alkene isosteres of Gramicidin S (i.e., hemigramicidin) were used as part of the targeting sequence. See FIG. 2 for a synthetic pathway for (E)-alkene isosteres and reference number 2 for the corresponding chemical structure. First, hydrozirconation of alkyne (FIG. 2, compound 1) with Cp$_2$ZrHCl is followed by transmetalation to Me$_2$Zn and the addition of N-Boc-isovaleraldimine. The resulting compound (not shown) was then worked up using a solution of tetrabutylammonium fluoride ("TBAF") and diethyl ether with a 74% yield. The resulting compound was then treated with acetic anhydride, triethylamine (TEA), and 4-N,N[1]-(dimethylamino) pyridine ("DMAP") to provide a mixture of diastereomeric allylic amides with a 94% yield which was separated by chromatography. Finally, the product was worked up with $K_2CO_3$ in methanol to yield the (E)-alkene, depicted as compound 2.

Figure 2:
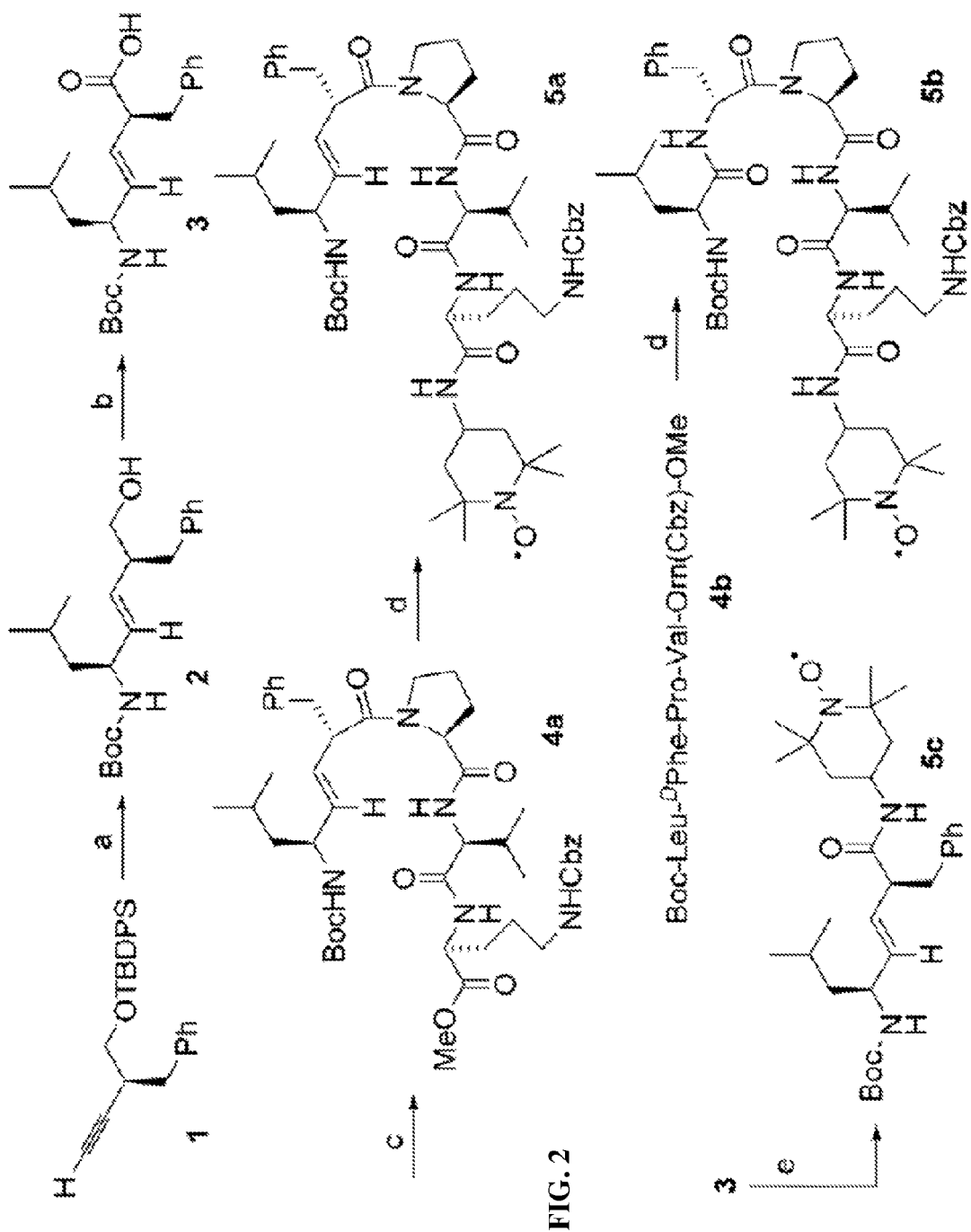
FIG. 2 depicts an example of a synthetic pathway for the TEMPO-hemigramicidin conjugates.

The (E)-alkene, depicted as compound 2 of FIG. 2, was then oxidized in a multi-step process to yield the compound 3 (FIG. 2)—an example of the (E)-alkene isostere.

Then, the compound 3 of FIG. 2 was then conjugated with the peptide H-Pro-Val-Orn (Cbz)-OMe using 1-ethyl-3-(3-dimethylaminopropyl carbodimide hydrochloride) (EDC) as a coupling agent. The peptide is an example of a suitable targeting sequence having affinity for the mitochondria of a cell. The resulting product is shown as compound 4a in FIG. 2. Saponification of compound 4a followed by coupling with 4-amino-TEMPO (4-AT) afforded the resulting conjugate shown as compound 5a in FIG. 2, in which the Leu-$^D$Phe peptide bond has been replaced with an (E)-alkene.

In an alternate embodiment, conjugates 5b in FIG. 2 was prepared by saponification and coupling of the peptide 4b (Boc-Leu-$^D$Phe-Pro-Val-Orn(Cbz)-OMe) with 4-AT. Similarly, conjugate 5c in FIG. 2 was prepared by coupling the (E)-alkene isostere as indicated as compound 3 in FIG. 2 with 4-AT. These peptide and peptide analogs are additional examples of suitable targeting sequences having an affinity to the mitochondria of a cell.

In another embodiment of the invention, peptide isosteres may be employed as the conjugate. Among the suitable peptide isosteres are trisubstituted (E)-alkene peptide isosteres and cyclopropane peptide isosteres, as well as all imine addition products of hydro- or carbometalated internal and terminal alkynes for the synthesis of di and trisubstituted (E)-alkene and cyclopropane peptide isosteres. See Wipf et al. *Imine additions of internal alkynes for the synthesis of trisubstituted (E)-alkene and cyclopropane isosteres*, ADV. SYNTH. CATAL. 347, 1605-1613 (2005). These peptide mimetics have been found to act as β-turn promoters. See Wipf et al. *Convergent Approach to (E)-Alkene and Cyclopropane Peptide Isosteres*, Organic Letters, VOL. 7, No. 103-106 (2005).

As is known to one ordinarily skilled in the art, nitroxide and nitroxide derivatives, including TEMPOL and associated TEMPO derivatives are stable radicals that can withstand biological environments. Therefore, the presence of the 4-amino-TEMPO or the TEMPOL "payload" within the mitochondria membrane can serve as an effective and efficient electron scavenger of the ROS being produced within the membrane.

MATERIALS AND METHODS

EXAMPLES

Materials. All chemicals were from SIGMA-ALDRICH (St Louis, Mo.) unless otherwise noted. Heparin, ketamine HCl and sodium pentobarbital were from ABBOTT LABORATORIES (North Chicago, Ill.). Dulbecco's modified Eagle medium ("DMEM") was from BIOWHITTAKER (Walkersville, Md.). Fetal bovine serum (FBS; <0.05 endotoxin units/ml) was from HYCLONE (Logan, Utah). Pyrogen-free sterile normal saline solution was from BAXTER (Deerfield, Ill.).

General. All moisture-sensitive reactions were performed using syringe-septum cap techniques under an N2 atmosphere and all glassware was dried in an oven at 150° C. for 2 h prior to use. Reactions carried out at −78° C. employed a $CO_2$-acetone bath. Tetrahydrofuran (THF) was distilled over sodium/benzophenone ketyl; $CH_2Cl_2$, toluene and $Et_3N$ were distilled from $CaH_2$. $Me_2Zn$ was purchased from ALDRICH COMPANY.

Reactions were monitored by thin layer chromatography ("TLC") analysis (EM SCIENCE pre-coated silica gel 60 F254 plates, 250 μm layer thickness) and visualization was accomplished with a 254 nm UV light and by staining with a Vaughn's reagent (4.8 g $(NH_4)_6Mo7O_{24}.4H_2O$, 0.2 g $Ce(SO_4)_2.4H_2O$ in 10 mL conc. $H_2SO_4$ and 90 mL $H_2O$). Flash chromatography on $SiO_2$ was used to purify the crude reaction mixtures.

Melting points were determined using a LABORATORY DEVICES Mel-Temp II. Infrared spectra were determined on a NICOLET Avatar 360 FT-IR spectrometer. Mass spectra were obtained on a WATERS Autospec double focusing mass spectrometer ("EI") or a WATERS Q-Tof mass spectrometer ("ESI"). LC-MS data were obtained on an Agilent 1100 instrument, using a WATERS Xterra MS CH 3.5 μm RP column (4.6×100 mm).

Synthesis, Example I. Prepared as a colorless oil (FIG. 2, compound 1) according to the literature procedure, see Edmonds, M. K. et al. *Design and Synthesis of a Conformationally Restricted Trans Peptide Isostere Based on the Bioactive Conformations of Saquinavir and Nelfinavir* J. ORG. CHEM. 66:3747 (2001); see also Wipf P. et al., *Convergent Approach to (E)-Alkene and Cyclopropane Peptide Isosteres* ORG. LETT. 7:103 (2005); see also Xiao, J. et al., *Electrostatic versus Steric Effects in Peptidomimicry: Synthesis and Secondary Structure Analysis of Gramicidin S Analogues with (E)-Alkene Peptide Isosteres* J. AM. CHEM. SOC. 127: 5742 (2005).

A solution of 2.20 g (5.52 mmol) of compound 1 (FIG. 2) in 20.0 mL of dry $CH_2Cl_2$ was treated at room temperature with 1.85 g (7.17 mmol) of $Cp_2ZrHCl$. The reaction mixture was stirred at room temperature for 5 min, $CH_2Cl_2$ was removed in vacuo and 20.0 mL of toluene was added. The resulting yellow solution was cooled to −78° C. and treated over a period of 30 min with 2.76 mL (5.52 mmol) of $Me_2Zn$ (2.0 M solution in toluene). The solution was stirred at −78° C. for 30 min, warmed to 0° C. over a period of 5 min and treated in one portion with 2.05 g (11.1 mmol) of N-Boc-isovaleraldimine, see Edmonds, M. K. et al. *Design and Synthesis of a Conformationally Restricted Trans Peptide Isostere Based on the Bioactive Conformations of Saquinavir and Nelfinavir* J. ORG. CHEM. 66:3747 (2001); see also Wipf P. et al., *Convergent Approach to (E)-Alkene and Cyclopropane Peptide Isosteres* J. ORG. LETT. 7:103 (2005); see also Xiao et al., *Electrostatic versus Steric Effects in Peptidomimicry: Synthesis and Secondary Structure Analysis of Gramicidin S Analogues with (E)-Alkene Peptide Isosteres* J. AM. CHEM. SOC. 127:5742 (2005).

The resulting mixture was stirred at 0° C. for 2 h, quenched with saturated $NH_4Cl$, diluted with EtOAc, filtered through a thin pad of Celite, and extracted with EtOAc. The organic layer was dried ($MgSO_4$), concentrated in vacuo, and purified by chromatography on $SiO_2$ (20:1, hexane/EtOAc) to yield 3.13 g (97%) as a colorless, oily 1:1 mixture of diastereomers.

A solution of 4.19 g (7.15 mmol) of product in 100 mL of dry tetrahydrofuran ("THF") was treated at 0° C. with 9.30 mL (9.30 mmol) of tetrabutylammoniumflouride (TBAF, 1.0 M solution in THF). The reaction mixture was stirred at room temperature for 20 h, diluted with EtOAc, and washed with brine. The organic layer was dried ($MgSO_4$), concentrated in vacuo, and purified by chromatography on $SiO_2$ (4:1, hexane/EtOAc) to yield 1.89 g (76%) as a light yellowish, foamy 1:1 mixture of diastereomers.

A solution of 1.86 g (5.23 mmol) of product in 40.0 mL of dry CH$_2$Cl$_2$ was treated at 0° C. with 1.46 mL (10.5 mmol) of triethylamine ("TEA"), 2.02 mL (21.4 mmol) of Ac$_2$O, and 63.9 mg (0.523 mmol) of 4-N,N$^1$-(dimethylamino) pyridine ("DMAP"). The reaction mixture was stirred at 0° C. for 15 min and at room temperature for 3 h, diluted with EtOAc, and washed with brine. The organic layer was dried (MgSO$_4$), concentrated in vacuo, and purified by chromatography on SiO$_2$ (20:1, hexane/Et$_2$O) to yield 1.97 g (94%) of acetic acid (2S)-benzyl-(5R)-tert-butoxycarbonylamino-7-methyloct-(3E)-enyl ester (807 mg, 38.7%), acetic acid (2S)-benzyl-(5S)-tert-butoxycarbonylamino-7-methyloct-(3E)-enyl ester (826 mg, 39.6%), and a mixture of the aforementioned species (337 mg, 16.2%).

A solution of 350 mg (0.899 mmol) of acetic acid (2S)-benzyl-(5S)-tert-butoxycarbonylamino-7-methyloct-(3E)-enyl ester in 8.00 mL of MeOH was treated at 0° C. with 62.0 mg (0.449 mmol) of K$_2$CO$_3$. The reaction mixture was stirred at 0° C. for 1 h and at room temperature for an additional 4 h, diluted with EtOAc, and ashed with H$_2$O. The organic layer was dried (MgSO$_4$), concentrated in vacuo, and purified by chromatography on SiO$_2$ (4:1, hexane/EtOAc) to yield 312 mg (quant.) of compound 2 (FIG. 2) as a colorless oil.

A solution of 23.0 mg (66.2 µmol) of compound 2 (FIG. 2) in 2.00 mL of dry CH$_2$Cl$_2$ was treated at 0° C. with 42.1 mg (99.3 µmol) of Dess-Martin Periodinane. The reaction mixture was stirred at 0° C. for 1 h and at room temperature for an additional 4 h, quenched with saturated Na$_2$S$_2$O$_3$ in a saturated NaHCO$_3$ solution, stirred for 30 min at room temperature, and extracted with CH$_2$Cl$_2$. The organic layer was dried (Na$_2$SO$_4$), concentrated in vacuo to give a colorless foam and subsequently dissolved in 3.00 mL of THF, and treated at 0° C. with 300 µL (600 µmol) of 2-methyl-2-butene (2.0 M solution in THF) followed by another solution of 18.0 mg (199 µmol) of NaClO$_2$ and 18.2 mg (132 µmol) of NaH$_2$PO$_4$.H$_2$O in 3.00 mL of H$_2$O. The reaction mixture was stirred at 0° C. for 1 h and at room temperature for an additional 3 h, extracted with EtOAc, and washed with H$_2$O. The organic layer was dried (Na$_2$SO$_4$) and concentrated in vacuo to yield compound 3 (FIG. 2) as a crude colorless foam that was used for the next step without purification.

A solution of crude compound 3 (FIG. 2) (66.2 µmol) in 3.00 mL of CHCl$_3$ was treated at 0° C. with 10.7 mg (79.2 µmol) of 1-hydroxybenzotrizole ("HOBt") and 14.0 mg (73.0 µmol) of 1-ethyl-3-(3-dimethylaminopropyl) carbodimide hydrochloride ("EDC"), followed by a solution of 62.9 mg (132 µmol) of H-Pro-Val-Orn(Cbz)-OMc, see Edmonds, M. K. et al. *Design and Synthesis of a Conformationally Restricted Trans Peptide Isostere Based on the Bioactive Conformations of Saquinavir and Nelfinavir* J. ORG. CHEM. 66:3747 (2001); see also Wipf P. et al., *Convergent Approach to (E)-Alkene and Cyclopropane Peptide Isosteres* J. ORG. LETT. 7:103 (2005); see also Xiao, J. et al., *Electrostatic versus Steric Effects in Peptidomimicry: Synthesis and Secondary Structure Analysis of Gramicidin S Analogues with (E)-Alkene Peptide Isosteres* J. AM. CHEM. SOC. 127:5742 (2005), in 1.00 mL of CHCl$_3$ and 0.8 mg (6.6 µmol) of DMAP. The reaction mixture was stirred at room temperature for 2 d, diluted with CHCl$_3$, and washed with H$_2$O. The organic layer was dried (Na$_2$SO$_4$), concentrated in vacuo, and purified by chromatography on SiO$_2$ (from 2:1, hexanes/EtOAc to 20:1, CHCl$_3$/MeOH) to yield 51.3 mg (94%) of compound 4a (FIG. 2) as a colorless foam.

A solution of 53.7 mg (65.5 µmol) of compound 4a (FIG. 2) in 2.00 mL of MeOH was treated at 0° C. with 655 µL (655 µmol) of 1 N NaOH. The reaction mixture was stirred at room temperature for 6 h, and treated with 655 µL (655 µmol) of 1 N HCl. The solution was extracted with CHCl$_3$ and the organic layer was dried (Na$_2$SO$_4$) and concentrated in vacuo to give the crude acid as a colorless form. This acid was dissolved in 5.00 mL of CHCl$_3$ and treated at room temperature with 10.6 mg (78.4 µmol) of HOBt, 15.1 mg (78.8 µmol) of EDC, 20.2 mg (118 µmol) of 4-amino-TEMPO and 8.0 mg (65.5 µmol) of DMAP. The reaction mixture was stirred at room temperature for 36 h, diluted with CHCl$_3$, and washed with H$_2$O. The organic layer was dried (Na$_2$SO$_4$), concentrated in vacuo, and purified by chromatography on SiO$_2$ (from 1:1, hexane/EtOAc to 20:1, CHCl$_3$/MeOH) to yield 62.0 mg (99%) of compound 5a (FIG. 2) as a colorless solid. The following characterization data were obtained: LC-MS (Rt 8.81 min, linear gradient 70% to 95% CH$_3$CN (H$_2$O) in 10 min, 0.4 mL/min; m/z=959.5 [M+H]$^+$, 981.5 [M+Na]$^+$) and HRMS (ESI) m/z calculated for C$_{53}$H$_{80}$N$_7$O$_9$Na (M+Na) 981.5915. found 981.5956.

A solution of 60.0 mg (71.7 µmol) of compound 4b (FIG. 2), see Tamaki, M. et al. I. BULL. CHEM. SOC. JPN, 66:3113 (1993), in 2.15 mL of MeOH was treated at room temperature with 717 tL (717 µmol) of 1 N NaOH. The reaction mixture was stirred at room temperature for 5 h, and treated at 0° C. with 717 µL (717 µmol) of 1 N HCl. The solution was extracted with CHCl$_3$ and the organic layer was dried (Na$_2$SO$_4$) and concentrated in vacuo to give the crude acid as colorless foam. The acid was dissolved in 6.04 mL of CHCl$_3$ and treated at room temperature with 11.6 mg (85.8 µmol) of HOBt, 16.5 mg (85.1 µmol) of EDC, 18.5 mg (108 µmol) of 4-amino-TEMPO and 8.8 mg (72.0 µmol) of DMAP. The reaction mixture was stirred at room temperature for 20 h, diluted with CHCl$_3$, and washed with H$_2$O. The organic layer was dried (Na$_2$SO$_4$), concentrated in vacuo, and purified by chromatography on SiO$_2$ (from 2:1, hexane/EtOAc; to 20:1, CHCl$_3$/MeOH) to yield 69.6 mg (99%) of compound 5b (FIG. 2) as a yellowish solid. The following characterization data were obtained: LC-MS (Rt 7.02 min, linear gradient 70% to 95% CH$_3$CN (H$_2$O) in 10 min, 0.4 mL/min; m/z=976.5 [M+H]', 998.4 [M+Na]$^+$) and HRMS (ESI) m/z calculated for C$_{52}$H$_{79}$N$_8$O$_{10}$Na (M+Na) 998.5817. found 998.5774.

A solution of crude compound 3 (FIG. 2) (40.3 µmol) in 3.00 mL of CH$_2$Cl$_2$ was treated at 0° C. with 10.4 mg (60.7 µmol) of 4-amino-TEMPO, 7.7 mg (40.2 µmol) of EDC, and 5.4 mg (44.2 µmol) of DMAP. The reaction mixture was stirred at room temperature for 20 h, diluted with CHCl$_3$, and washed with H$_2$O. The organic layer was dried (Na$_2$SO$_4$), concentrated in vacuo, and purified by chromatography on SiO$_2$ (from 4:1 to 1:1, hexane/EtOAc) to yield 18.8 mg (91%) of compound 5c (FIG. 2) as a yellowish solid. The following characterization data were obtained: LC-MS (Rt 7.01 min, linear gradient 70% to 95% CH$_3$CN (H$_2$O) in 10 min, 0.4 mL/min; m/z=537.3 [M+Na]$^+$) and HRMS (ESI) in/z calculated for C30H48N3O4Na (M+Na) 537.3543. found 537.3509.

Determination of intracellular superoxide radicals Oxidation-dependent fluorogenic dye, dihydroethidium ("DHE", Molecular Probes) was used to evaluate intracellular production of superoxide radicals. DHE is cell permeable and, in the presence of superoxide, is oxidized to fluorescent ethidium which intercalates into DNA. The fluorescence of ethidium was measured using a FACscan (BECTON-DICKINSON, Rutherford, N.J.) flow cytometer, equipped with a 488-nm argon ion laser and supplied with the Cell Quest software. Mean fluorescence intensity from 10,000 cells were acquired using a 585-nm bandpass filter (FL-2 channel).

Determination of intracellular ATP levels. Cells were incubated with 10 µm of compound 5a (FIG. 2) for indicated periods of time (2, 4, 6, 12, and 14 h). At the end of incubation, cells were collected and the content of intracellular ATP was determined using a bioluminescent somatic cell assay kit (SIGMA, St. Louis, Mass.). As a positive control, cells were incubated with 2 mM of 2-dexy-glucose, a glucose analogue which competitively inhibits cellular uptake and utilization of glucose, for 12 and 14 h.

Cells. Caco-2BBe human enterocyte-like epithelial cells were obtained from the AMERICAN TYPE CULTURE COLLECTION (Manassas, Va.). Cells were routinely maintained at 37° C. in under a humidified atmosphere containing 8% CO2 in air. The culture medium was DMEM supplemented with 10% FBS, non-essential amino acids supplement (SIGMA-ALDRICH catalogue #M7145), sodium pyruvate (2 mM), streptomycin (0.1 mg/ml), penicillin G (100 U/ml) and human transferrin (0.01 mg/ml). The culture medium was changed 3 times per week.

Surgical procedures to obtain vascular access. All study protocols using rats followed the guidelines for the use of experimental animals of the US National Institutes of Health and were approved by the Institutional Animal Care and Use Committee at the University of Pittsburgh.

Male specific pathogen-free Sprague Dawley rats (CHARLES RIVER LABORATORIES, Wilmington, Mass.), weighing 150-250 g, were housed in a temperature-controlled environment with a 12-h light/dark cycle. The rats had free access to food and water. For experiments, rats were anesthetized with intramuscular ketamine HCl (30 mg/kg) and intraperitoneal sodium pentobarbital (35 mg/kg). Animals were kept in a supine position during the experiments. Lidocaine (0.5 ml of a 0.5% solution) was injected subcutaneously to provide local anesthesia at surgical cut-down sites. In order to secure the airway, a tracheotomy was performed and polyethylene tubing (PE 240; BECTON-DICKINSON, Sparks, Md.) was introduced into the trachea. Animals were allowed to breathe spontaneously.

The right femoral artery was cannulated with polyethylene tubing (PE 10). This catheter was attached to a pressure transducer that allowed instantaneous measurement of mean arterial pressure (MAP) during the experiment. For experiments using the pressure-controlled hemorrhagic shock (HS) model, the right jugular vein was exposed, ligated distally, and cannulated with polyethylene tubing (PE 10) in order to withdraw blood. For experiments using the volume-controlled hemorrhagic shock (HS) model, the jugular catheter was used to infuse the resuscitation solution and the right femoral vein, which was cannulated with a silicon catheter (CHRONIC-CATH, NORFOLK MEDICAL, Skokie, Ill.), was used to withdraw blood.

All animals were instrumented within 30 min. Heparin (500 U/kg) was administered immediately after instrumentation through the femoral vein. Animals were placed in a thermal blanket to maintain their body temperature at 37° C. The positioning of the different devices aforementioned was checked postmortem.

Intestinal mucosal permeability assay. Animals were allowed access to water but not food for 24 h prior to the experiment in order to decrease the volume of intestinal contents. The rats were instrumented as described above.

A midline laparotomy was performed and the small intestine was exteriorized from the duodenojejunal junction to the ileocecal valve. A small incision was made on the antimesenteric aspect of the proximal small intestine and saline solution (1.5 ml) was injected. The bowel was ligated proximally and distally to the incision with 4-0 silk (LOOK, Reading, Pa.).

The small intestine was compressed gently in aboral direction along its length to displace intestinal contents into the colon. Starting 5 cm from the ileocecal valve, the ileum was partitioned into six contiguous water-tight segments. Each segment was 3 cm long and was bounded proximally and distally by constricting circumferential 4-0 silk sutures. Care was taken to ensure that the vascular supply to intestine was not compromised, and each segment was well-perfused.

Two randomly selected segments in each rat were injected with 0.3 ml of vehicle and served as "no treatment" controls. In order to fill the segments, a small incision was made and the solution was injected using a Teflon catheter (ABBOCATH 16Ga, ABBOTT LABORATORIES).

The remaining four other segments were injected with solutions containing either 4-hydroxy-2,2,6,6-tetramethylpiperidine-N-oxyl (TEMPOL) or one of the Gramicidin S-based compounds. Four different final concentrations of TEMPOL in normal saline were evaluated: 0.1, 1, 5 and 20 mM. The hemigramicidin-based compounds were dissolved in a mixture of dimethylsulfoxide (DMSO) and normal saline (1:99 v/v) and injected at final concentrations of 0.1, 1, 10 or 100 µM.

After the segments were loaded with saline or the test compounds, the bowel was replaced inside the peritoneal cavity and the abdominal incision was temporarily closed using Backhaus forceps.

After a 5 min stabilization period, hemorrhagic shock was induced by withdrawing blood via the jugular catheter. MAP was maintained at 30±3 mm Hg for 2 hours. The shed blood was re-infused as needed to maintain MAP within the desired range.

After 2 h of shock, the animals were euthanized with an intracardiac KCl bolus injection. The ileum was rapidly excised from the ileocecal valve to the most proximal gut segment. The tips of each segment were discarded. In order to assay caspases 3 and 7 activity and phospholipids peroxidation, mucosa samples were collected from gut segments immediately after hemorrhage and stored at −80° C. For permeability measurements, each segment was converted into an everted gut sac, as previously described by Wattanasirichaigoon et al., see Wattanasirichaigoon, S. et al., *Effect of mesenteric ischemia and reperfusion or hemorrhagic shock on intestinal mucosal permeability and ATP content in rats*, SHOCK, 12:127-133 (1999).

Briefly, as per the Wattanasirichaigoon protocol referenced above, the sacs were prepared in ice-cold modified Krebs-Henseleit bicarbonate buffer ("KHBB"), pH 7.4. One end of the gut segment was ligated with a 4-0 silk suture; the segment was then everted onto a thin plastic rod. The resulting gut sac was mounted on a Teflon catheter (Abbocath 16GA, Abbot Laboratories) connected to a 3 ml plastic syringe containing 1.5 ml of KHBB. The sac was suspended in a beaker containing KHBB plus fluorescein-isothiocyanate labeled dextran (average molecular mass 4 kDa; FD4; 0.1 mg/ml). This solution was maintained at 37° C., and oxygenated by bubbling with a gas mixture ($O_2$ 95%/$CO_2$ 5%). After 30 min, the fluid within the gut sac was collected. The samples were cleared by centrifugation at 2000 g for 5 min.

Fluorescence of FD4 in the solution inside the beaker and within each gut sac was measured using a fluorescence spectrophotometer (LS-50, PERKIN-ELMER, Palo Alto, Calif.) at an excitation wavelength of 492 nm and an emission wavelength of 515 nm. Mucosal permeability was expressed as a clearance normalized by the length of the gut sac with units of $nL \cdot min^{-1} \cdot cm^2$, as previously described, see Yang, R. et al., *Ethyl pyruvate modulates inflammatory gene expression in mice subjected to hemorrhagic shock*, AM. J. PHYSIOL. GASTROINTEST. LIVER PHYSIOL. 283:G212-G22 (2002).

Results for a specific experimental condition (i.e., specific test compound at a single concentration) were expressed as relative change in permeability calculated according to this equation: Relative change in permeability (%)=($CH_{Hs\ exp}$−$C_{normal}$)/$C_{Hs\ cont}$−$C_{normal}$)×100, where $C_{Hs\ exp}$ is the clearance of FD4 measured for a gut segment loaded with the experimental compound, $C_{normal}$ is the clearance of FD4 measured in 6 gut segments from 3 normal animals not subjected to hemorrhagic shock, and $C_{Hs\ cont}$ is the mean clearance of FD4 measured in 2 gut segments filled with vehicle from the same animal used to measure $C_{HS\ exp}$.

Measurement of permeability of Caco-2 monolayers. Caco-$2_{BBe}$ cells were plated at a density of $5 \times 10^4$ cells/well on permeable filters (0.4 μm pore size) in 12-well bicameral chambers (TRANSWELL, COSTAR, Corning, N.Y.). After 21 to 24 days, paracellular permeability was determined by measuring the apical-to-basolateral clearance of FD4.

Briefly, the medium on the basolateral side was replaced with control medium or medium containing menadione (50 μM final). Medium containing FD4 (25 mg/ml) was applied to the apical chamber. In some cases, one of the gramicidin S-based compounds, XJB-5-131, also was added to the apical side at final concentrations of 0.1, 1, 10 or 100 μM. After 6 hours of incubation, the medium was aspirated from both compartments. Permeability of the monolayers was expressed as a clearance ($pL \cdot h^{-1} \cdot cm^{-2}$), see Han, X. et al., *Proinflammatory cytokines cause NO dependent and independent changes in expression and localization of tight junction proteins in intestinal epithelial cells*, SHOCK 19:229-237 (2003).

Caspases 3 and 7 activity assay. Caspases 3 and 7 activity was measured using a commercially available assay kit, CASPASE GLO™ 3/7 assay kit (PROMEGA, Madison, Wis.). Briefly, 50 μl of rat gut mucosa homogenate (20 jug protein) was mixed with 50 μl of Caspase-G1oTM reagent and incubated at room temperature for 1 hour. At the end of incubation period, the luminescence of each sample was measured using a plate reading chemiluminometer (ML1000, DYNATECH LABORATORIES, Horsham, Pa.). Activity of caspases 3 and 7 was expressed as luminescence intensity (arbitrary units per mg protein). Protein concentrations were determined using the BIORAD assay (BIO-RAD LABORATORIES, Inc., Hercules, Calif.).

Assay for peroxidation of phospholipids. Gut mucosal samples were homogenized. Lipids were extracted from homogenates using the Folch procedure, see M. Lees and G. H. Sloan-Stanley, *A simple method for isolation and purification of total lipids from animal tissue*, J. BIOL. CHEM. 226:497-509 (1957), and resolved by 2D HPTLC (High Performance Thin Layer Chromatography) as previously described, see Kagan, V. E. et al., *A role for oxidative stress in apoptosis: Oxidation and externalization of phosphatidylserine is required for macrophage clearance of cell undergoing Fas-mediated apoptosis*, J. IMMUMOL. 169:487-489 (2002). Spots of phospholipids were scraped from HPTLC plates and phospholipids were extracted from silica. Lipid phosphorus was determined by a micro-method, see Bottcher, C. J. F. et al., *A rapid and sensitive sub-micro phosphorus determination*, ANAL. CHIM. ACTA 24: 203-204 (1961).

Oxidized phospholipids were hydrolyzed by pancreatic phospholipase A2 (2 U/μl) in 25 mM phosphate buffer containing 1 mM $CaCl_2$, 0.5 mM EDTA and 0.5 mM sodium dodecyl sulfate (SDS) (pH 8.0, at room temperature for 30 min). Fatty acid hydroperoxides formed were determined by fluorescence HPLC of resorufin stoichiometrically formed during their microperoxidase 11-catalized reduction in presence of Amplex Red (for 40 min at 4° C.) (8). Fluorescence HPLC (ECLIPSE XDB-C18 column, 5 μm, 150×4.6 mm, mobile phase was composed of 25 mM disodium phosphate buffer (pH 7.0)/methanol (60:40 v/v); excitation wavelength 560 nm, emission wavelength 590 nm) was performed on a SHIMADZU LC-100AT HPLC system equipped with fluorescence detector (RF-10Ax1) and autosampler (SIL-10AD).

Survival of rats subjected to volume-controlled hemorrhagic shock. Following surgical preparation and a 5-min stabilization period to obtain baseline readings, rats were subjected to hemorrhagic shock. Bleeding was carried out in 2 phases.

Initially, 21 ml/kg of blood was withdrawn over 20 min. Immediately thereafter, an additional 12.5 ml/kg of blood was withdrawn over 40 min. Thus, hemorrhage occurred over a total period of 60 min and the total blood loss was 33.5 ml/kg or approximately 55% of the total blood volume. Rats were randomly assigned to receive XJB-5-131 (2 μmol/kg) or its vehicle, a 33:67 (v/v) mixture of DMSO and normal saline. XJB-5-131 solution or vehicle alone was administered as a continuous infusion during the last 20 min of the hemorrhage period. The total volume of fluid infused was 2.8 ml/kg and it was administered intravenously using a syringe pump (KD100, KD SCIENTIFIC, New Hope, Pa.). Rats were observed for 6 hours or until expiration (defined by apnea for >1 min). At the end of the 6 hour observation period, animals that were still alive were euthanized with an overdose of KCl.

Blood pressure was recorded continuously using a commercial strain-gauge transducer, amplifier, and monitor (S90603a, SPACELABS, Redmond, Wash.). Blood samples (0.5 ml) were collected from the jugular vein at the beginning of hemorrhage (baseline), at the end of hemorrhage (shock) and at the end of resuscitation (resuscitation). Hemoglobin concentration [Hb], lactate and glucose concentration were determined using an auto-analyzer (Model ABL 725, RADIOMETER COPENHAGEN, Westlake, Ohio).

Data presentation and statistics. All variables are presented as means+Standard Error Mean (SEM). Statistical significance of differences among groups was determined using ANOVA (analysis of variance) and LSD (Least Significant Difference) tests, or Kruskal-Wallis and Mann-Whitney tests as appropriate. Survival data were analyzed using the log-rank test. Significance was declared for p values less than 0.05.

Example I

Selective delivery of TEMPO to mitochondria could lead to therapeutically beneficial reduction of ROS; therefore, investigation of the use of conjugates of 4-amino-TEMPO ("4-AT") was explored. In order to selective target the mitochondria, a targeting sequence using the membrane active antibiotic Gramicidin S ("GS") as well as corresponding alkene isosteres, shown in FIGS. 1 and 2. Accordingly, using the Gramicidin S peptidyl fragments and alkene isosteres as "anchors," the TEMPO "payload" could be guided into the mitochondria.

The Leu-$^D$Phe-Pro-Val-Orn fragment of Gramicidin S was used as a targeting sequence. Alkene isosteres such as (E)-alkene isosteres of this segment of Gramicidin S (i.e., hemigramicidin) were used as part of the targeting sequence. See FIG. 3 for the synthetic pathway for (E)-alkene isosteres and compound 3 for the corresponding chemical structure. The (E)-alkene as depicted in compound 2 of FIG. 2 was then converted in a multi-step process to yield the structure as depicted in compound 3 as an example of the (E)-alkene isostere.

Then, the compound depicted as compound 3 of FIG. 2 was conjugated with the tripeptide H-Pro-Val-Orn(Cbz)-OMe using 1-ethyl-3-(3-dimethylaminopropyl) carbodiimide hydrochloride ("EDC") as a coupling agent. The tripeptide is an example of a suitable targeting sequence having affinity for the mitochondria of a cell. The resulting product is shown as compound 4a in FIG. 2. Saponification of compound 4a followed by coupling with 4-amino-TEMPO ("4-AT") afforded the resulting conjugates shown as compound 5a in FIG. 2, in which the Leu-$^D$Phe peptide bond has been replaced with an (E)-alkene.

Figure 3:
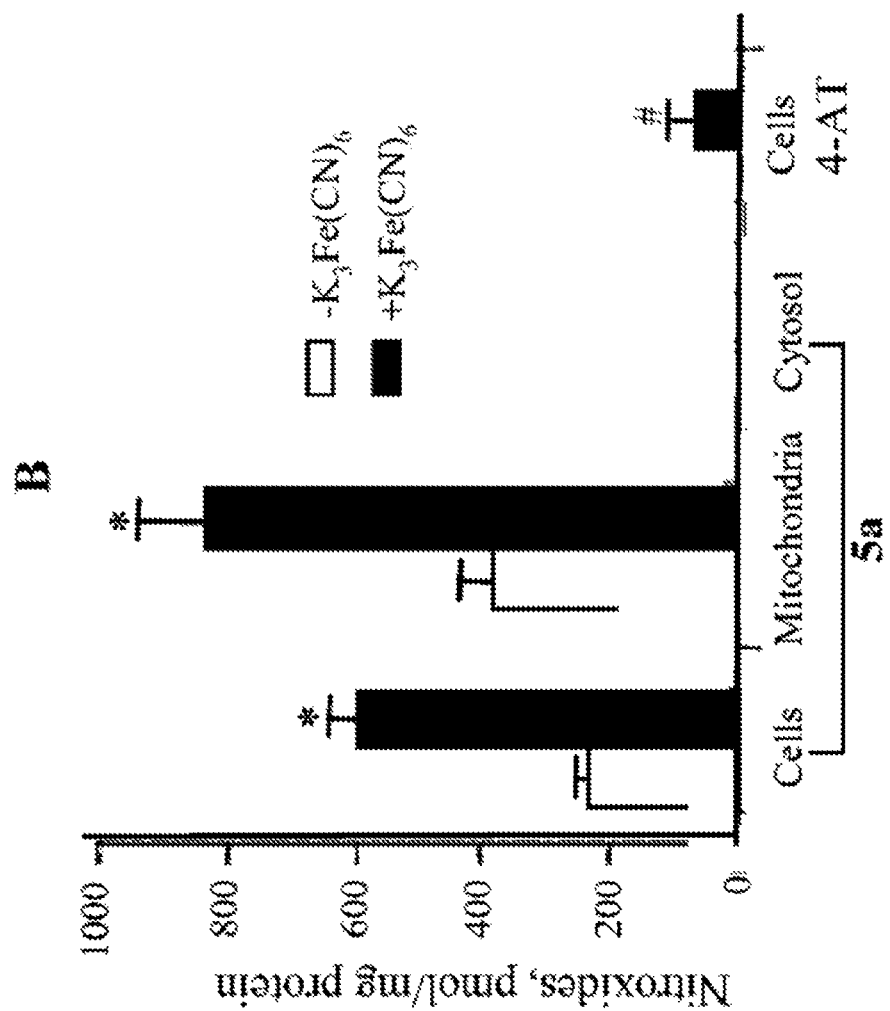
FIG. 3 shows (A) an EPR-based analysis of integration and (B) reduction of nitroxide Gramicidin S peptidyl-TEMPO conjugates in MECs.
Figure 3:
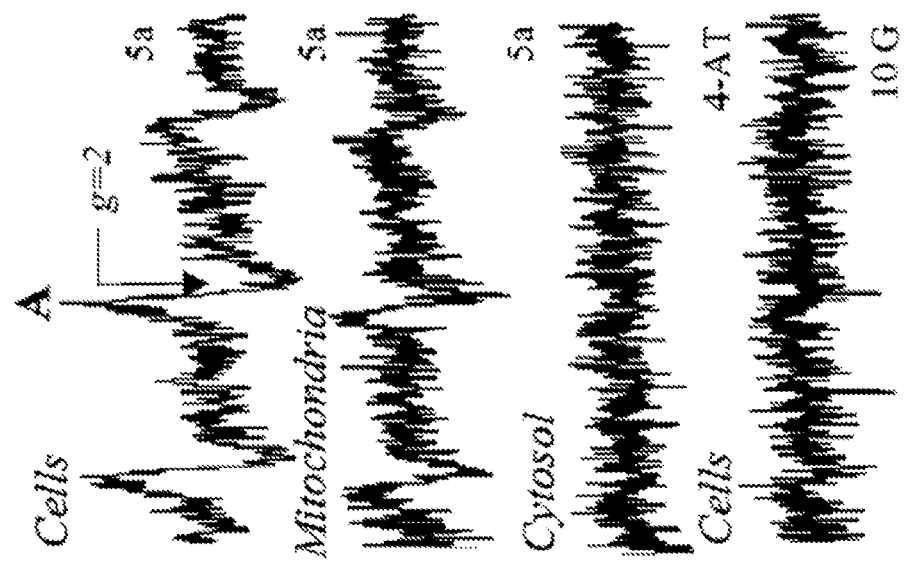

In an alternate embodiment, conjugates 5b and 5c in FIG. 2 by coupling the peptide 4b (Boc-Leu-$^D$Phe-Pro-Val-Orn (Cbz)-OMe) and the (E)-alkene isostere as indicated as compound 3 in FIG. 2 to 4-AT. The peptide is another example of a suitable targeting sequence having an affinity with the mitochondria of a cell.

Electron paramagnetic resonance ("EPR") spectroscopy was used to monitor the cellular delivery of compounds 5a and 5b shown in FIG. 2 in mouse embryonic cells ("MEC").

The following conditions were used during the EPR-based analysis of the integration and reduction of nitroxide Gramicidin S-peptidyl conjugates in MECs. The MECs at a concentration of 10 million MECs per mL were incubated with 10 μM of 4-AT and compound 5a, respectively. Recovered nitroxide radicals in whole cells, mitochondria, and cytosol fractions were resuspended in phosphate buffer saline ("PBS") in the presence and absence, respectively, of 2 μM $K_3Fe(CN)_6$. In brief, FIG. 3, panel A shows a representative EPR spectra of compound 5a in different fractions of MECs in the presence of $K_3Fe(CN)_6$. Further, FIG. 3, panel B shows an assessment of integrated nitroxides.

Distinctive characteristic triplet signals of nitroxide radicals were detected in MECs incubated with 10 μM of compound 5a (FIG. 2) as well as in mitochondria isolated from these cells. The cytosolic function did not elicit EPR signals of nitroxide radicals; similar results were observed with conjugate 5b (FIG. 2) (data not shown).

Incubation of MECs with compound 5a (FIG. 2) resulted in integration and one-electron reduction of compound 5a, as evidenced by a significant increase in magnitude of the EPR signal intensity upon addition of a one-electron oxidant, ferricyanide (FIG. 3, panel B). (Note: EPR results for incubation of MECs with 5b are not shown in FIG. 3; however, EPR results for 5b were similar when compared to 5a). In contrast to 5a and 5b, however, 4-amino-TEMPO (4-AT) did not effectively permeate cells or the mitochondria, as shown by the absence of significant amplitude change in the EPR results for 4-AT.

The ability of 5a, 5b (FIG. 2), and 4-AT to prevent intracellular superoxide generation by flow cytometric monitoring of oxidation of dihydroehtidium ("DHE") to a fluorescent ethidium was tested. The ability of 5a, 5b, and 4-AT to protect cells against apoptosis triggered by actinomycin D ("ActD") was also tested. MECs were pretreated with 10 μM 4-AT, 5a, or 5b then incubated with ActD at a concentration of 100 ng/mL. It was found that 5a and 5b completely inhibited nearly two-fold intracellular superoxide generation in MECs (see FIG. 5, panel A). 4-AT had no effect on the superoxide production in MECs.

Apoptotic cell responses were documented using three biomarkers: (1) externalization of phosphatidylserine ("PS") on the cell surface (by flow cytometry using an FITC-labeled PS-binding protein, annexin V, see FIG. 5, panels B and E); (2) activation of caspase-3 by cleavage of the Z-DEVD-AMC substrate (see FIG. 5, panel C), and, (3) DNA fragmentation by flow cytometry of propidiium iodide stained DNA (see FIG. 5, panel D).

Phosphatidylserine ("PS") is an acidic phospholipid located exclusively on the inner leaflet of the plasma membrane; exposure of PS on the cell surface is characteristic of cell apoptosis. Externalization of PS was analyzed by flow cytometry using an annexin V kit. Cells were harvested by trypsinization at the end of incubation and then stained with annexin V-FITC and propidium iodide ("PS"). Ten thousand cell events were collected on a FACScan flow cytometer. Cells that annexin V-positive and PI-negative were considered apoptotic.

Activation of capase-3, a cystein protease only activated in the execution phase of apoptosis, was determined using an EnzChek capsase-3 assay kit.

Further, calcium and magnesium dependent nucleases are activated that degrade DNA during apoptosis. These DNA fragments are eluted, stained with propidium iodide and analyzed using flow cytometry. A cell population with decreased DNA content was considered a fraction of apoptotic cells.

Figure 5:
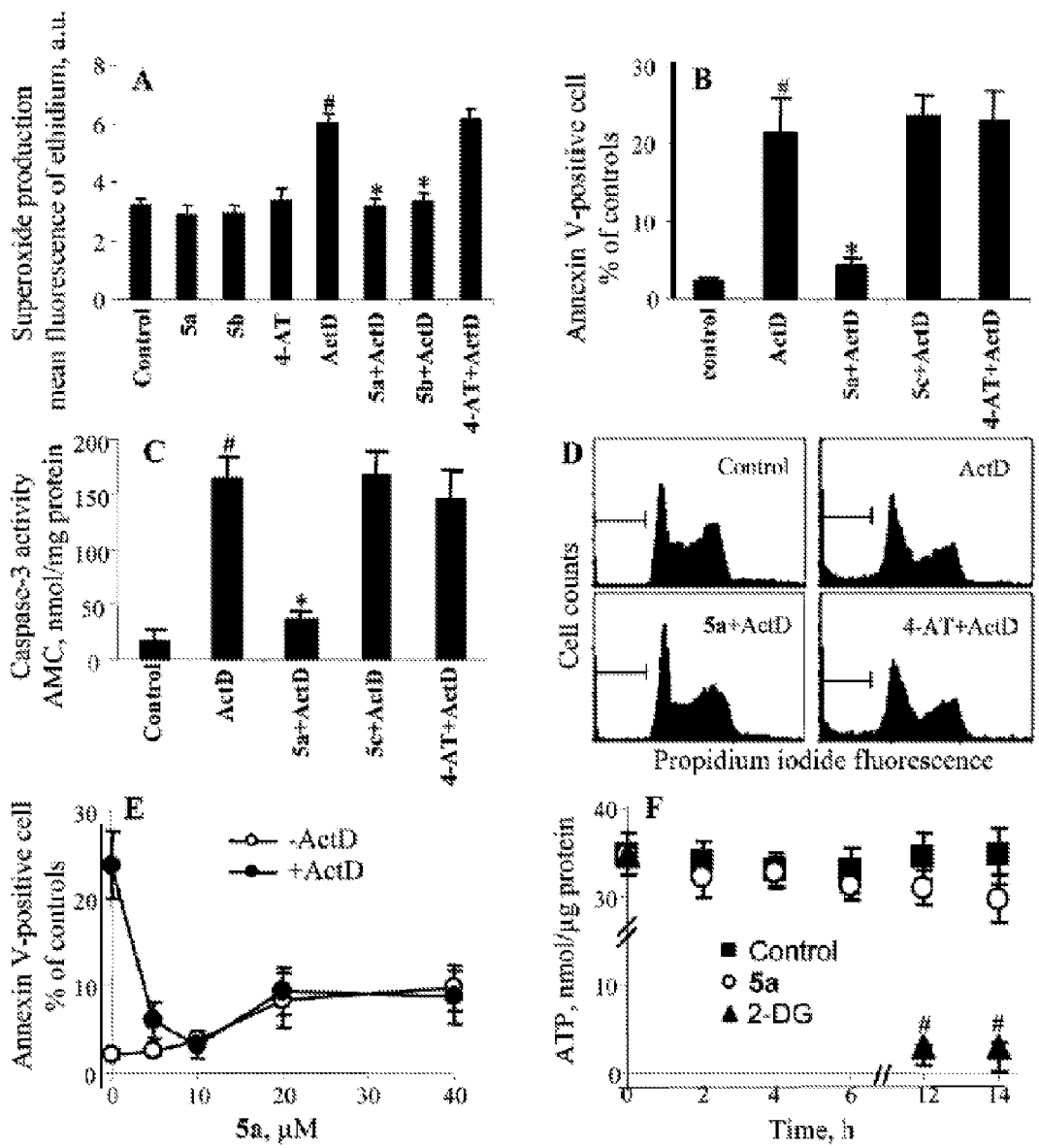
FIG. 5 shows graphical representations of the effect of nitroxide conjugates on ActD-induced apoptosis. Panel A is a graphical representation of superoxide production based upon mean fluorescence intensity from 10,000 ileal cells. Panel B is a graphical representation of phosphatidylserine (PS) externalization as indicated by the percentage of annexin V-positive cells. Panel C is a graphical representation of caspase-3 activity as indicated by amount of its specific substrate present, Z-DVED-AMC, in nmol/mg protein. Panel D is a graphical representation of DNA fragmentation as indicated by propidium iodide fluorescence. Panel E is a graphical representation of PS externalization at different concentrations of the compound 5a. Panel F is a graphical representation of adenosine triphosphate (ATP) levels in mitochondria in the presence or absence of 5a or 2-deoxyglucose.

Anti-apoptotic effects of compounds 5a and 5b were observed at relatively low concentrations of 10 μM. Compounds 5a and 5b (FIG. 3) reduced the number of annexin V-positive cells as shown in FIG. 5, panel B, prevented caspase-3 activation as shown in FIG. 5, panel C, and prevented DNA fragmentation as shown in FIG. 5, panel D. At concentrations in excess of 10 μM, both 5a and 5b were either less protective or exhibited cytotoxicity (FIG. 5, panel E). In contrast, 4-AT afforded no protection.

In contrast, compound 5c, which does not have a complete targeting moiety, was ineffective in protecting MECs against ActD-induced apoptosis (FIG. 5, panels B and C) at low concentrations. Accordingly, the hemigramicidin peptidyl targeting sequence is essential for anti-apoptotic activity of nitroxide conjugates such as those containing TEMPO.

Finally, the reduction of compounds 5a and 5b could also cause inhibition of mitochondrial oxidative phosphorylation, so the ATP levels of MECs treated with these compounds were tested. As is known to one ordinarily skilled in the art, ATP serves as the primary energy source in biological organisms; reduction of ATP levels would greatly impair normal cell function. ATP levels in MECs in the presence or absence of 5a or 2-deoxyglucose ("2-DG") were used as a positive control (see FIG. 5, panel F). At concentrations at which anti-apoptotic effects were maximal (~10 μM, FIG. 5, panel E), nitroxide conjugates did not cause significant changes in the cellular ATP level. Therefore, synthetic GS-peptidyl conjugates migrate into cells and mitochondria where they are reduced without affecting the ability of the mitochondria to produce ATP.

Example II

In an in vivo assay, the ileum of rats was divided into a series of well-vascularized components in a manner akin to links of sausage. The lumen of each ileal compartment was filled with a 3 μL aliquot of test solution. Two of the ileal compartments were filled with vehicle alone (i.e., a solution containing at least in part the TEMPO derivative). These two components served as internal controls to account for individualistic variations in the severity of shock or the response of the mucosa to the shock.

Using this assay system, eight compounds were evaluated as shown in FIG. 5: TEMPOL (FIG. 4A, panel A), one dipeptidic TEMPO analog (FIG. 4A, panel B—XJB-5-208), 3 hemigramicidin-TEMPO conjugates (FIG. 4B, panel C XJB- 5-125, 4C, panel E XJB-5-131, and 4D, panel G XJB-5-197), and 3 hemigramicidin compounds that do not have the TEMPO moiety (FIG. 4B, panel D—XJB-5-127, 4C, panel F—XJB-5-133, and 4D, panel H-XJB-5-194).

Hemorrhagic shock in rats leads to marked derangements in intestinal mucosal barrier function—in other words, the mucosal permeability of shocked intestinal segments was significantly greater than the permeability of segments from normal rats (52.3+0.5 versus 6.9+0.1 nL·min$^{-1}$·cm$^{-2}$, respectively; p<0.01), see Tuominen, E. K. J., *Phospholipid cytochrome c interaction: evidence for the extended lipid anchorage*, J. BIOL. CHEM., 277:8822-8826 (2002); also Wipf P. et al., *Mitochondria targeting of selective electron scavengers: synthesis and biological analysis of hemigramicidin-TEMPO conjugates*, J. AM. CHEM. SOC. 127:12460-12461. Accordingly, mice were subjected to 2 hours of shock (Mean Arterial Pressure ("MAP")=30 f 3 mm Hg), the gut segments were harvested and mucosal permeability to flourescein isothiocyanate-dextran ("FD4") measured ex vivo. Data in FIG. 4 are expressed as a percentage of the change permeability relative to that observed in simultaneously assayed control segments loaded during shock with normal saline solution.

Accordingly, intraluminal TEMPOL was used as a "positive control" for gut mucosal protection assay. TEMPOL concentrations >1 mM in the gut lumen ameliorated hemorrhagic shock-induced ileal mucosal hyperpermeability (FIG. 5, panel A). Two of the TEMPO conjugates, namely XJB-5-208 (FIG. 4A, panel B) and XJB-5-131 (FIG. 4B, panel C), also significantly ameliorated hemorrhagic shock-induced ileal mucosal hyperpermeability. The lowest effective concentration for XJB-5-208 (FIG. 4A, panel B) and XJB-5-131 (FIG. 4C, panel E) was 1 µM; i.e., both of these compounds were ~1000-fold more potent than TEMPOL. Two other compounds carrying the TEMPO payload, XJB-5-125 (FIG. 4B, panel C) and XJB-5-197 (FIG. 4D, panel G) failed to provide protection against gut barrier dysfunction induced by hemorrhage. XJB-5-133 (FIG. 4C, panel F) has the same (hemigramicidin-based) mitochondrial targeting moiety as XJB-5-131 (FIG. 4B, panel E) but lacks the TEMPO payload. It is noteworthy, therefore, that XJB-5-133 (FIG. 4C, panel F) did not afford protection from the development of ileal mucosal hyperpermeability.

Figure 4A:
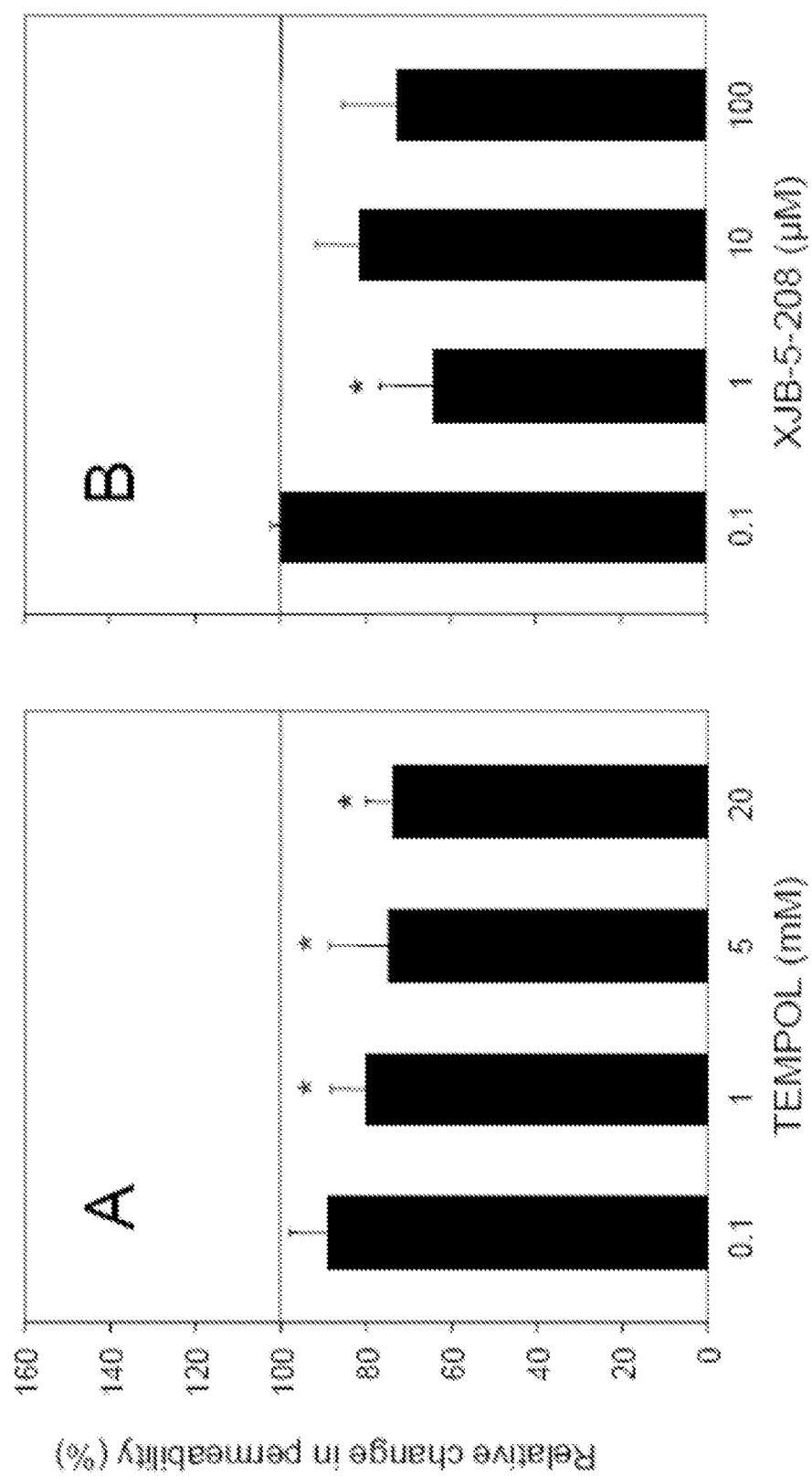
FIG. 4A-4D shows a flourescein isothiocyanate-dextran (FD4) read-out which reflects the effect of Gramicidin-S TEMPO conjugates on rat ileal mucosal permeability following profound hemorrhagic shock. Data are expressed as a percentage of the change permeability relative to that observed in simultaneously assayed control segments loaded during shock with normal saline solution.
Figure 4B:
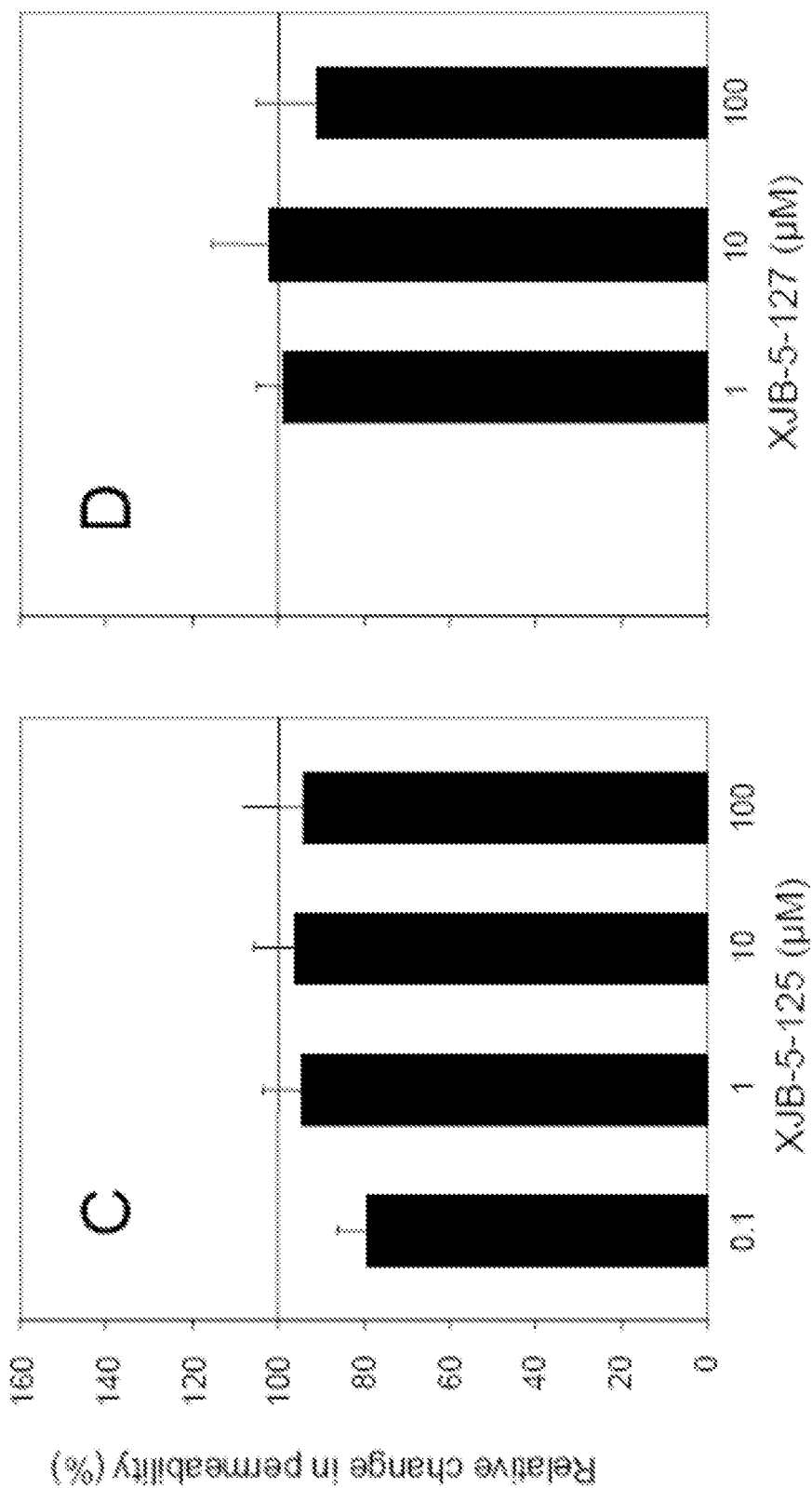
Figure 4C:
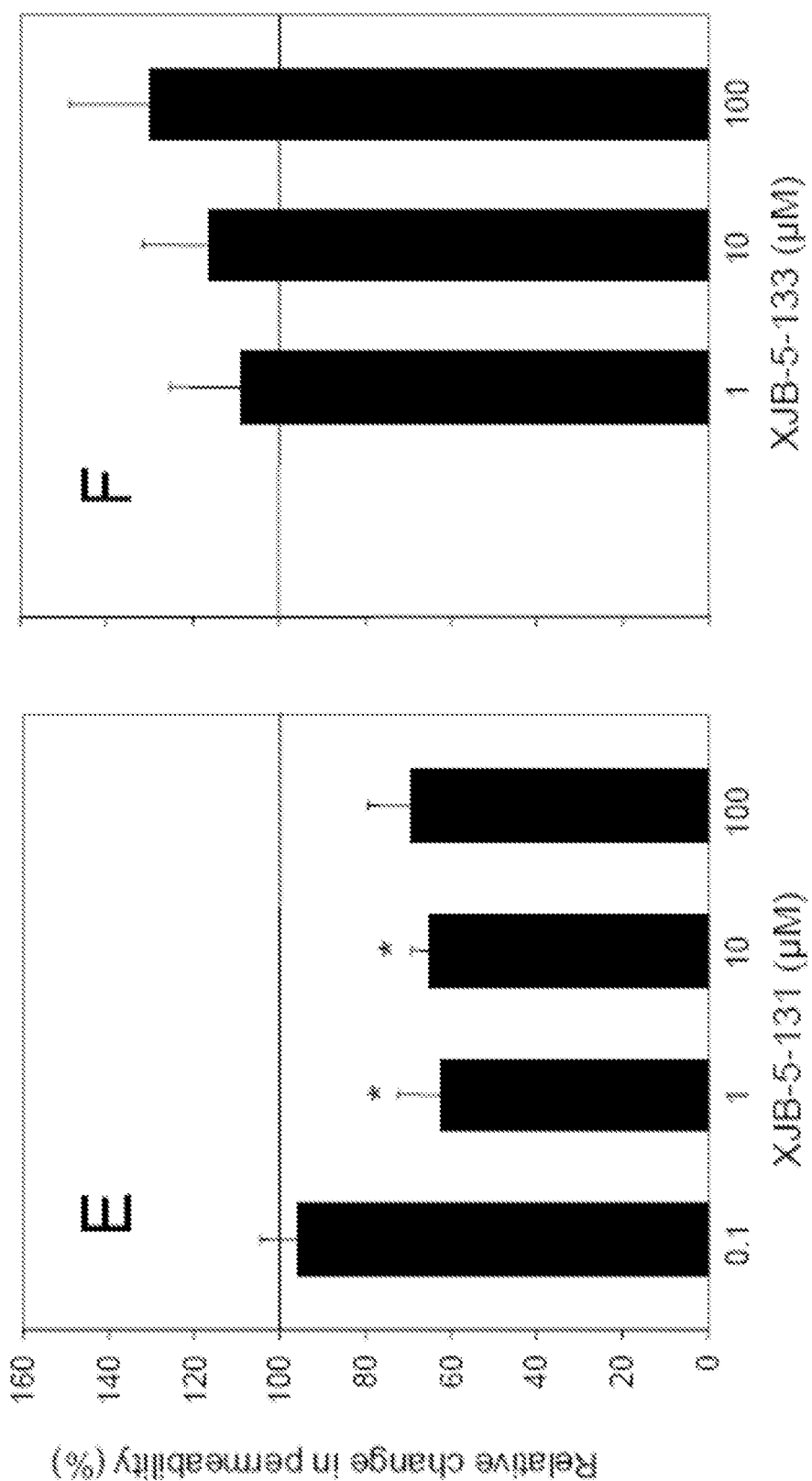
Figure 4D:
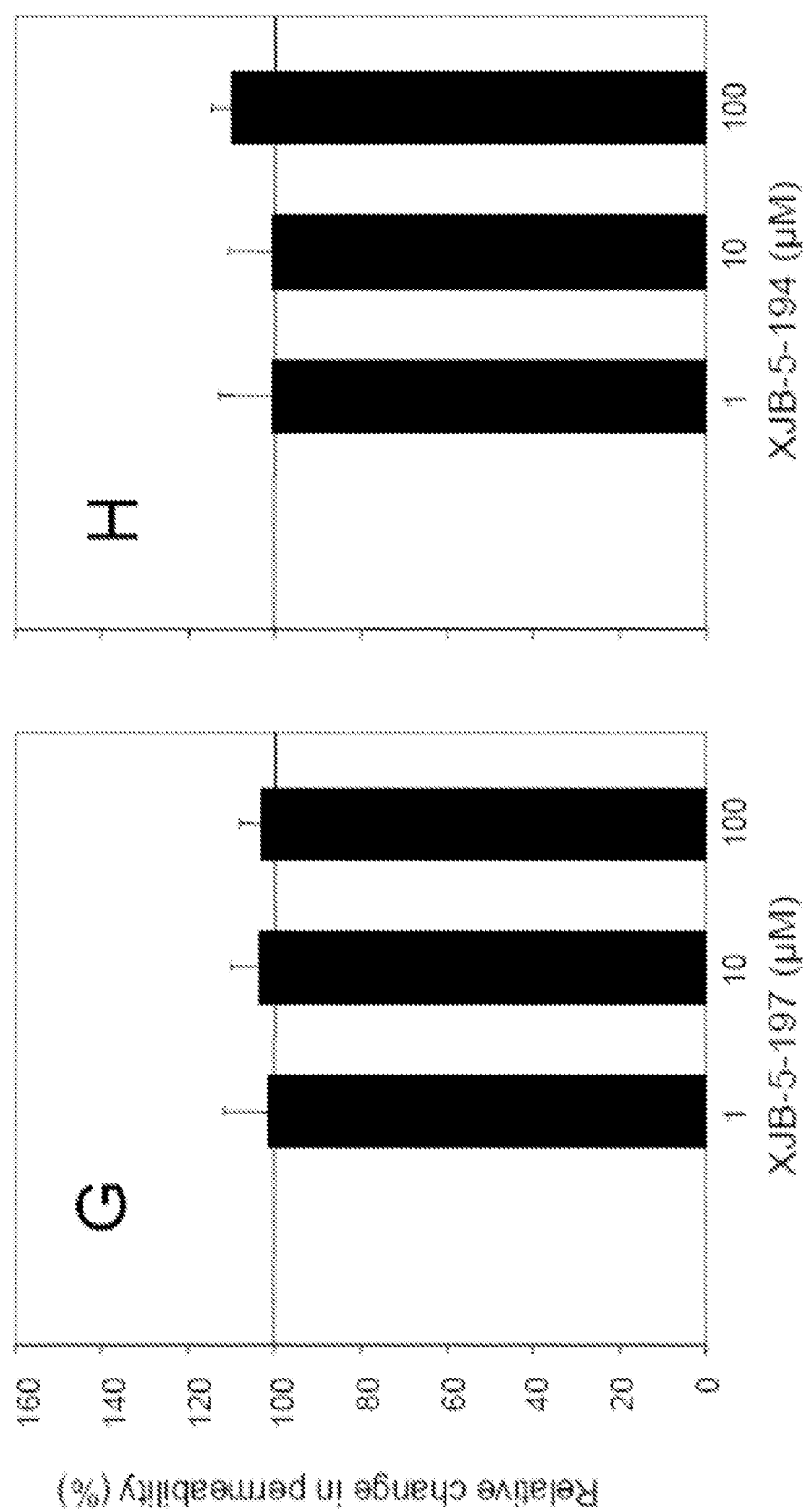

Ineffective as well were the two other hemigramicidin-based compounds that also lacked the TEMPO payload, XJB-5-127 (FIG. 4B, panel D) and XJB-5-194 (FIG. 4D, panel H). Of the compounds screened, XJB-5-131 (FIG. 4C, panel E) appeared to be the most effective, reducing hemorrhagic shock-induced mucosal hyperpermeability to approximately 60% of the control value.

Based upon the results as reflected in FIG. 4A-4D, both the TEMPO payload and the "anchoring" hemigramicidin fragment are requisite moieties that should be present in order for effective electron scavenging activity by the XJB-5-131 compound. Accordingly, it was found that XJB-5-131 ameliorates peroxidation of mitochondrial phosopholipids (i.e., ROS activity) in gut mucosa from rats subject to hemorrhagic shock.

In the subsequent series of in vivo studies, the affect of intraluminal XJB-5-131 on hemorrhage-induced peroxidation of phospholipids in intestinal mucosa was examined. Isolated segments of the ileum of rats were divided into a series of well-vascularized components in a manner akin to sausage and the lumen of each ileal compartment was filled with the same volume of test solution containing either vehicle or a 10 µM solution of XJB-5-131, which was previously indicated to be the most active of the hemigramicidin-TEMPO conjugates. In a preferred embodiment, 0.3 mL of test solution filled the lumen of each ileal compartment.

After two hours of HS, samples of ileal mucosa from the gut sacs filled with the vehicle and XJB-5-131 were obtained and compared with ileal mucosa of normal MECs. All samples were assayed with caspase 3 or caspase 7 activity as well as the peroxidation of phosphatidylcholine ("PC"), phosphatidylethanolamine ("PE"), phosphatidylserine ("PS"), and cardiolipin ("CL"), summarized in FIG. 6.

Figure 6:
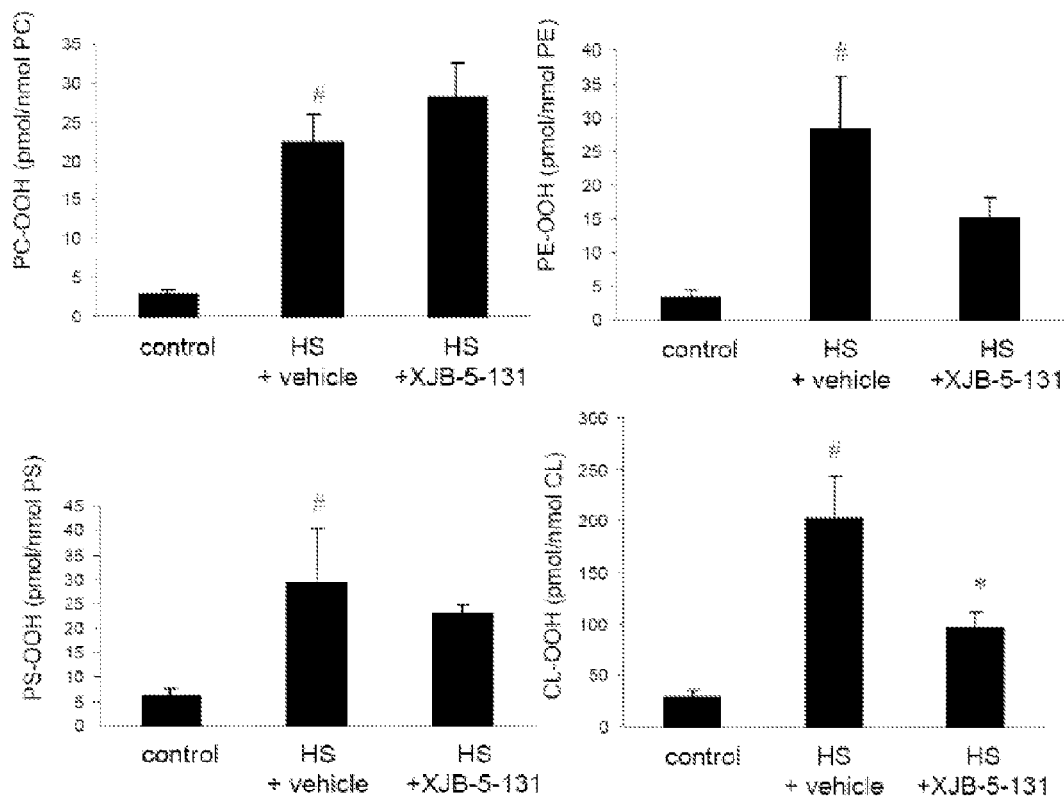
FIG. 6 illustrates the effects of intraluminal XJB-5-131 on hemorrhage-induced peroxidation of phospholipids in intestinal mucosa. The upper left panel is a graphical representation of the peroxidation of phosphatidylcholine ("PC"). The upper right panel is a graphical representation of peroxidation activity with respect to phosphatidylethanolamine ("PE"). The lower left panel is a graphical representation of peroxidation activity with respect to phosphatidylserine ("PS"). The lower right panel is a graphical representation of peroxidation activity with respect to cardiolipin ("CL").

As can be seen in FIG. 6, treatment with XJB-5-131 significantly ameliorated hemorrhage-induced peroxidation of CL, the only phospholipid tested found in mitochondria. However, treatment with XJB-5-131 only had a small effect on PE peroxidation and no effect on peroxidation of PC and PS. Based upon these trends, hemorrhagic shock is associated with substantial oxidative stress even in the absence of resuscitation. Further, this data also establishes that XJB-5-131 is an effective ROS scavenger as it localizes predominantly in mitochondria and protects CL from peroxidation.

Figure 7:
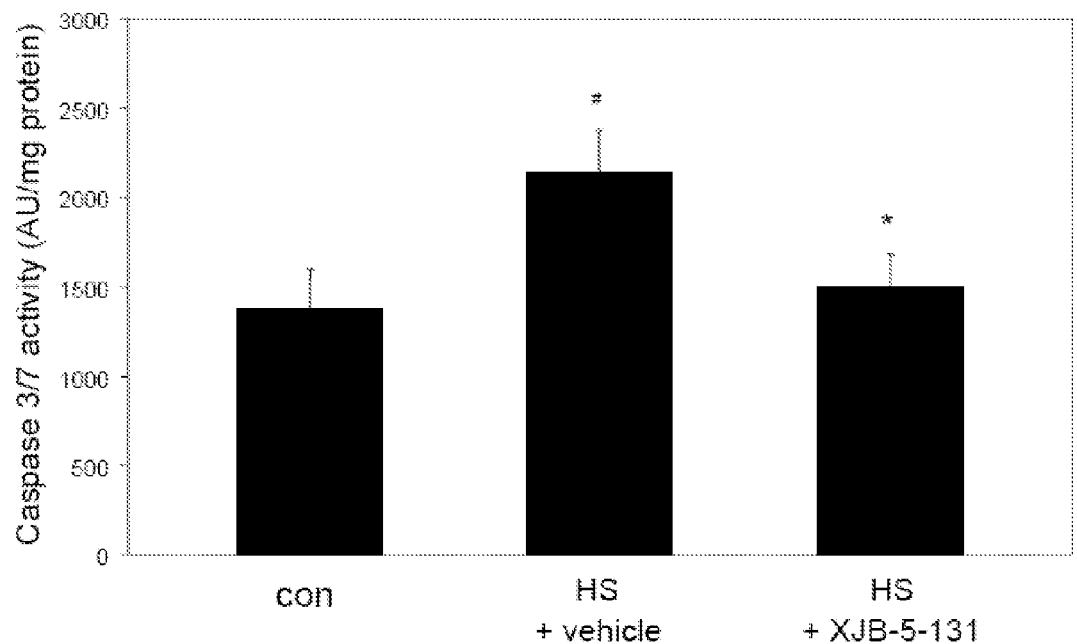
FIG. 7 is a graphical representation of caspase 3 and 7 activity that illustrates the effects of intraluminal XJB-5-131.

Relative to the activity measured in samples from normal animals, the activity of caspases 3 and 7 was markedly increased in vehicle-treated mucosal samples from hemorrhaged rats (FIG. 7). However, when the ileal segments were filled with XJB-5-131 solution instead of its vehicle, the level of caspase 3 and 7 activity after hemorrhagic shock was significantly decreased. Accordingly, hemorrhagic shock is associated with activation of pro-apoptotic pathways in gut mucosal cells. Moreover, the data support the view that this process is significantly ameliorated following mitochondrial treatment with XJB-5-131.

Example III

In another series of experiments, monolayers of enterocyte-like cells, Caco-2$_{BBe}$, were studied for physiological and pathophysiological purposes for determining intestinal barrier function. Just as with the prior Example I and II with respect to ROS exposure, the permeability of Caco-2$_{BBe}$ monolayers increases when the cells are incubated with the ROS, hydrogen peroxide, or menadione (a redox-cycling quinine that promotes the formation of superoxide anion radicals), see Baker, R. D. et al., *Polarized Caco-2 cells, Effect of reactive oxygen metabolites on enterocyte barrier function*, DIGESTIVE DIS. SCI. 40:510-518 (1995); also Banan, A. et al., *Activation of delta-isoform of protein kinase C is required for oxidant-induced disruption of both the microtubule cytoskeleton and permeability barrier of intestinal epithelia*, J. PHARMACOL. EXP. THER. 303:17-28 (2002).

Figure 8:
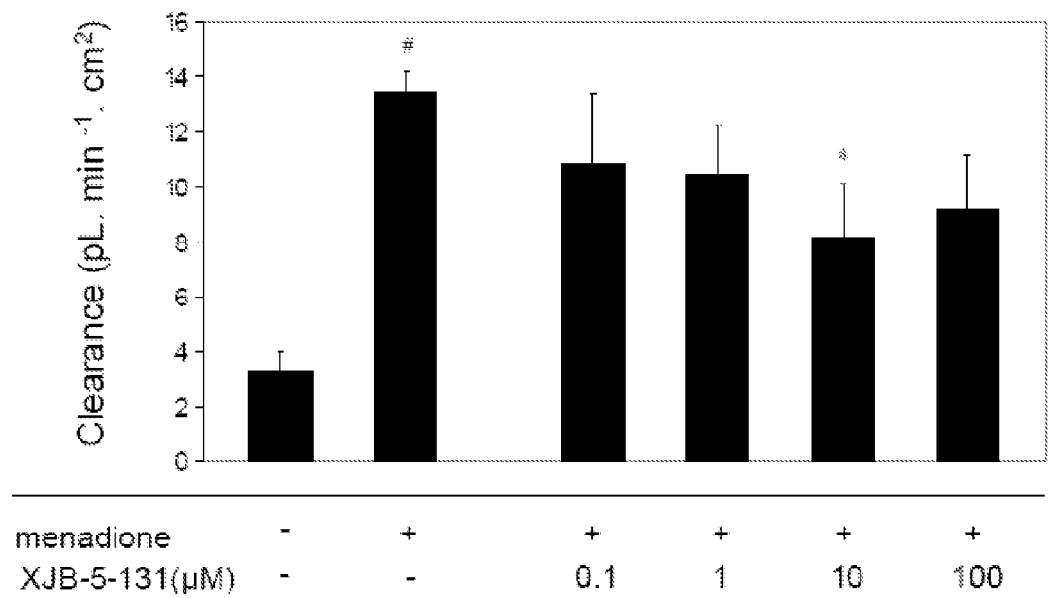
FIG. 8 is a graphical representation of permeability of XJB-5-131 with respect to Caco-2$_{BBe}$ human enterocyte-like monolayers subjected to oxidative stress. The permeability of the monolayers is expressed as a clearance (pL·h$^{-1}$·cm$^2$).

Due to the results with respect to XJB-5-131 and its amelioration of hemorrhage-induced CL peroxidation in mucosal cells in vivo (see aforementioned Example I and II), a possible treatment using XJB-5-131 was investigated to determine if menadione-induced epithelial hyperpermeability could be ameliorated in vitro. Consistent with the prior in vivo observations, Caco-2$_{BBe}$ monolayers were incubated in the absence and in the presence of menadione, respectively. After 6 hours, incubation of Caco-2$_{BBe}$ monolayers with menadione caused a marked increase in the apical-basolateral clearance of FD4 (FIG. 8). Treatment with 10 µM XJB-5-131 provided significant protection against menadione-induced hyperpermeability.

Example IV

As reflected by the above in vivo and in vitro studies, XJB-5-131 had significantly beneficial effects on several biochemical and physiological read-outs. Accordingly, systemic administration of XJB-5-131 was investigated with respect to whether it would prolong survival of patients subjected to profound periods of hemorrhagic shock with massive blood loss in the absence of standard resuscitation with blood and crystalloid solution. As in the above studies, rats were utilized as test patients.

A total of sixteen rats were tested in this study. Rats were treated with 2.8 ml/kg of vehicle or the same volume of XJB-5-131 solution during the final 20 min of the bleeding protocol. The total dose of XJB-5-131 infused was 2 µmol/kg. Following profound hemorrhagic shock consistent with the protocol described above for the prior studies, thirteen survived for at least 60 min and received the full dose of either XJB-5-131 solution or the vehicle, a 33:67 (v/v) mixture of DMSO and normal saline. As shown in Table 1, blood glucose, lactate and hemoglobin concentrations were similar in both groups at baseline and before and immediately after treatment. None of the between-group differences were statistically significant.

TABLE 1

| Parameter | Compound | Baseline | End of first phase of hemorrhage | End of second phase of hemorrhage |
|---|---|---|---|---|
| Blood glucose concentration (mg/dL) | Vehicle | 143 ± 5 | 255 ± 30 | 219 ± 26 |
| | XJB-5-131 | 134 ± 4 | 228 ± 24 | 201 ± 38 |
| Blood lactate concentration (mEq/L) | Vehicle | 1.8 ± 0.4 | 606 ± 0.8 | 5.9 ± 1.3 |
| | XJB-5-131 | 1.8 ± 0.2 | 5.7 ± 0.8 | 5.6 ± 1.2 |
| Blood Hb concentration (g/dL) | Vehicle | 12.7 ± 0.5 | 11.1 ± 0.3 | 9.4 ± 0.2 |
| | XJB-5-131 | 12.7 ± 0.3 | 10.7 ± 0.3 | 9.4 ± 0.3 |

Figure 9A:
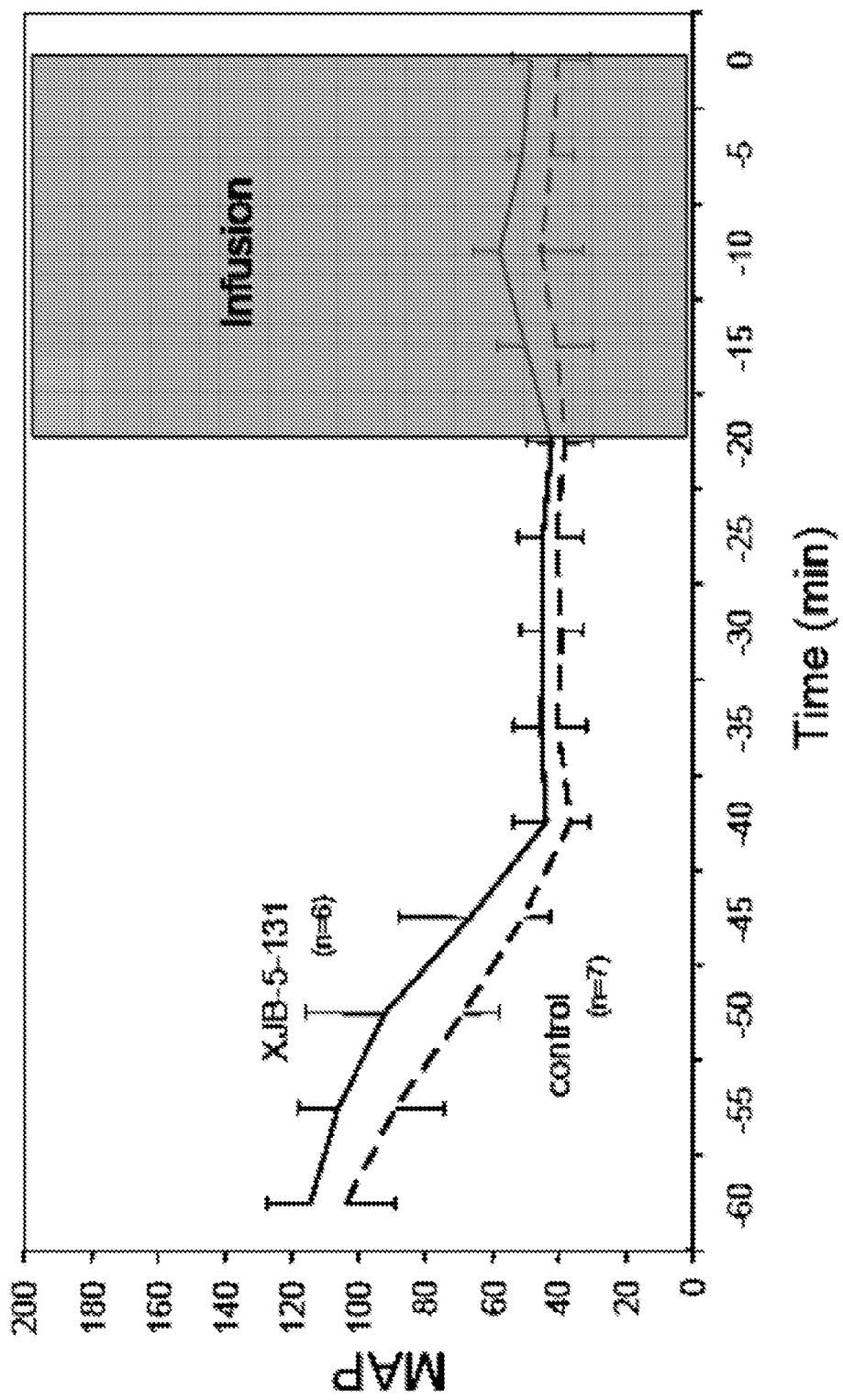
FIG. 9A-9B is a graphical representation of the effects of intravenous treatment with XJB-5-131 on MAP (mean arterial pressure, mm Hg) of rates subjected to volume controlled hemorrhagic shock.
Figure 9B:
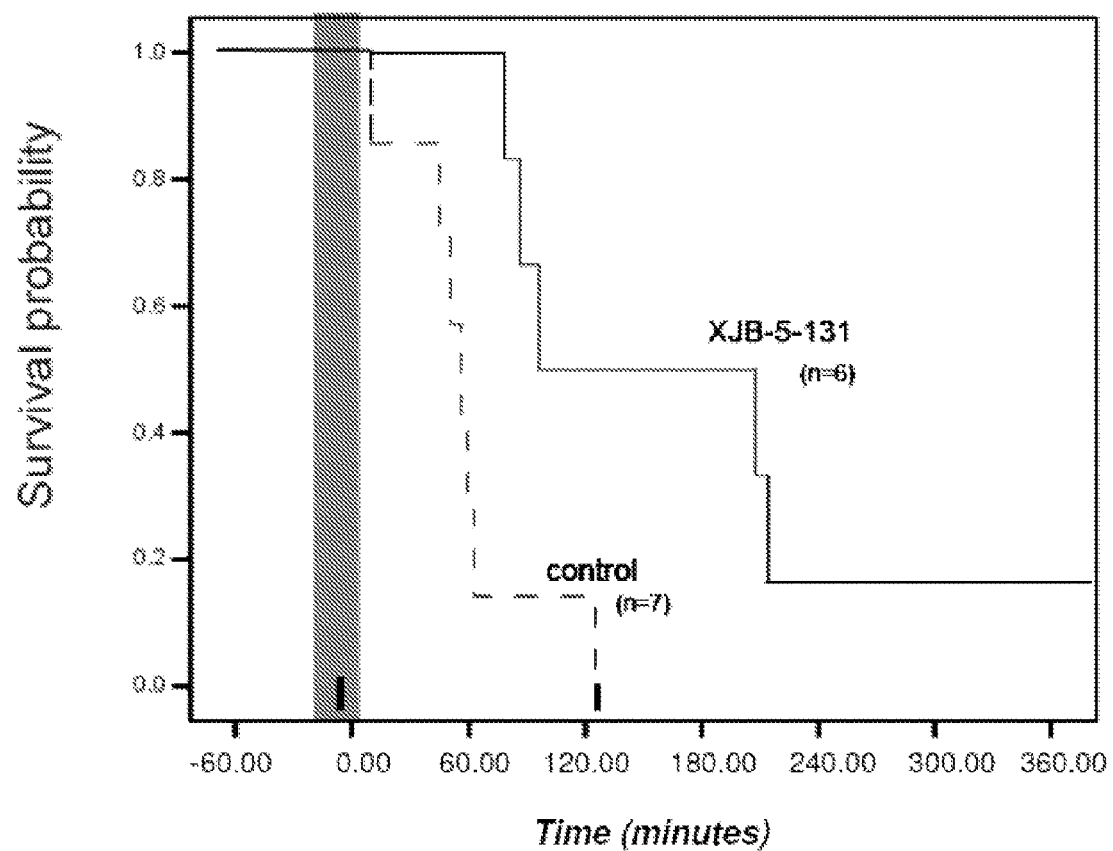

Shortly after treatment was started, mean arterial pressure ("MAP") increased slightly in both groups (see FIG. 9A). In both groups, mean arterial pressure ("MAP") decreased precipitously during the first phase of the hemorrhage protocol and remained nearly constant at 40 mm Hg during the beginning of the second phase. Six of the seven animals in the vehicle-treated (control) group died within one hour of the end of the bleeding protocol and all were dead within 125 minutes (FIG. 9B). Rats treated with intravenous XJB-5-131 survived significantly longer than those treated with the vehicle. Three of the six rats survived longer than 3 hours after completion of the hemorrhage protocol; one rat survived the whole 6 hour post-bleeding observation period (FIG. 9B).

Analysis

Accordingly, analysis of the XJB-5-131 studies indicate that exposure of the patient to the compound prolongs the period of time that patients can survive after losing large quantities of blood due to traumatic injuries or other catastrophes (e.g., rupture of an abdominal aortic aneurysm).

By extending the treatment window before irreversible shock develops, treatment in the field with XJB-5-131 might "buy" enough time to allow transport of more badly injured patients to locations where definitive care, including control of bleeding and resuscitation with blood products and non-sanguineous fluids, can be provided. The results using a rodent model of hemorrhagic shock also open up the possibility that drugs like XJB-5-131 might be beneficial in other conditions associated with marked tissue hypoperfusion, such as stroke and myocardial infarction.

The results presented here also support the general concept that mitochondrial targeting of ROS scavengers is a reasonable therapeutic strategy. Although previous studies have shown that treatment with TEMPOL is beneficial in rodent HS situations, a relatively large dose of the compound was required (30 mg/kg bolus+30 mg/kg per h). In contrast, treatment with a dose of XJB-5-131 that was about 300 fold smaller (~0.1 mg/kg) was clearly beneficial. The greater potency of XJB-5-131 as compared to TEMPOL presumably reflects the tendency of XJB-5-131 to localize in mitochondrial membranes, a key embodiment of the invention. As indicated in Example I, two hemigramicidin-4-amino-TEMPO conjugates (namely XJB-5-208 and XJB-5-131, see FIG. 2) are concentrated in the mitochondria of cultures mouse embryonic cells following incubation with solutions of the compounds.

Further, the use of XJB-5-131 significantly prolonged the survival of the rats subjected to massive blood loss, even though the animals were not resuscitated with either blood or other non-sanguineous fluids and they remained profoundly hypotensive.

In light of the above, synthetic hemigramicidin peptidyl-TEMPO conjugates permeate through the cell membrane and also the mitochondrial membrane where they act as free radical scavengers for ROS such as, but not limited to, superoxide anion radicals. The conjugates are then reduced within the mitochondria by electron-transport proteins which are involved with the cellular respiration pathway, thereby coupling the decoupled ROS species. These conjugates also have the advantage, as discussed above, of being anti-apoptotic, especially in the case of compounds such as 5a and 5b.

By effectively reducing the amount of ROS species, a patient's condition, including an illness or other medical condition, may be ameliorated and, in some cases, survival may be prolonged as described in the Example IV study. Examples of such conditions, including diseases and other medical conditions, include (but are not limited to) the following medical conditions which include diseases and conditions: myocardial ischemia and reperfusion (e.g., after angioplasty and stenting for management of unstable angina or myocardial infarction), solid organ (lung liver, kidney, pancreas, intestine, heart) transplantation, hemorrhagic shock, septic shock, stroke, tissue damage due to ionizing radiation, lung injury, acute respiratory distress syndrome (ARDS), necrotizing pancreatitis, and necrotizing enterocolitis.

Example V

In a further embodiment of the invention, a composition for scavenging radicals in a mitochondrial membrane comprises a radical scavenging agent or an NOS inhibitor and a membrane active peptidyl fragment having a high affinity with the mitochondrial membrane. The membrane active peptidyl fragment preferably has a property selected from the group consisting of antioxidant, radioprotective, protective, anti-apoptotic, therapeutic, ameliorative, NOS antagonist and combinations thereof.

In a related embodiment, with respect to compounds with antibiotic properties, it is generally preferable to employ compounds whose mode of action includes bacterial wall targets.

In a preferred embodiment, the membrane active compound is preferably selected from the group consisting of bacitracins, gramicidins, valinomycins, enniatins, alamethicins, beauvericin, serratomolide, sporidesmolide, tyrocidins, polymyxins, monamycins, and lissoclinum peptides.

In a related embodiment, the NOS antagonist is selected from the group consisting of XJB-5-234 (a), XJB-5-133 (b), XJB-5-241 (c), and XJB-5-127 (d):

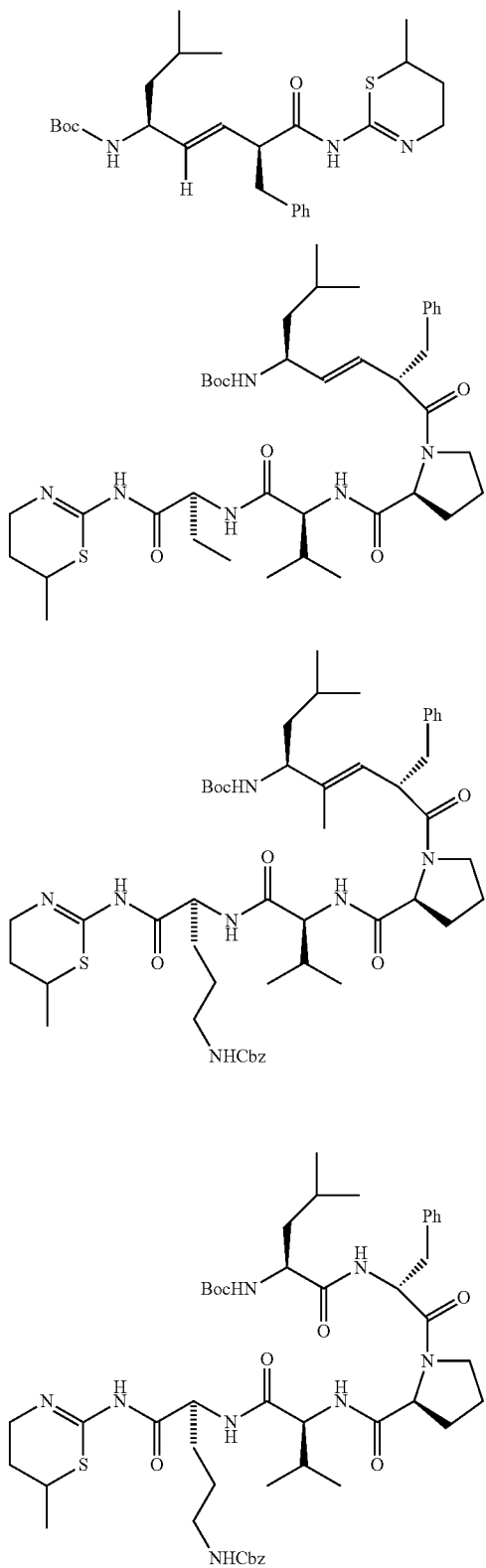

Example VI

The following examples provide protocols for additional cargo usable in the present invention for compounds which serve as NOS antagonists.

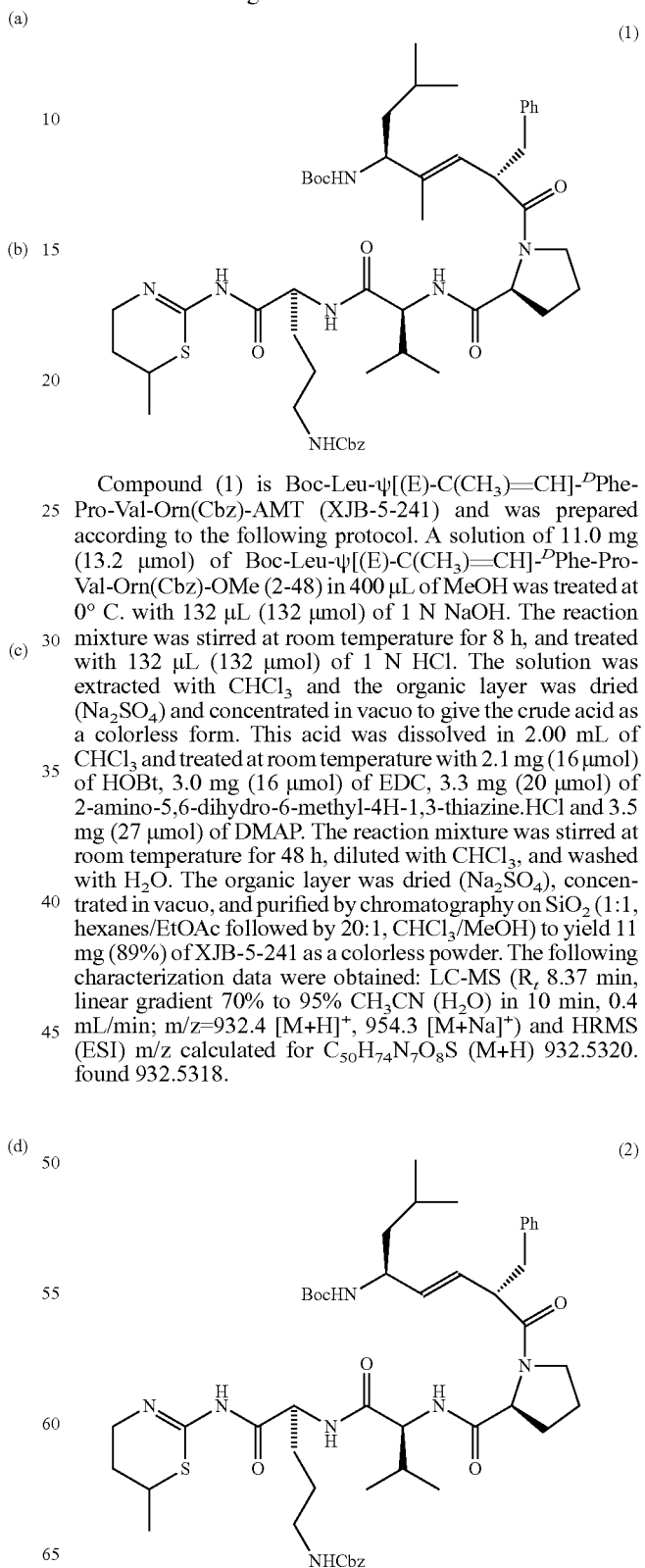

Compound (1) is Boc-Leu-ψ[(E)-C(CH$_3$)=CH]-$^D$Phe-Pro-Val-Orn(Cbz)-AMT (XJB-5-241) and was prepared according to the following protocol. A solution of 11.0 mg (13.2 μmol) of Boc-Leu-ψ[(E)-C(CH$_3$)=CH]-$^D$Phe-Pro-Val-Orn(Cbz)-OMe (2-48) in 400 μL of MeOH was treated at 0° C. with 132 μL (132 μmol) of 1 N NaOH. The reaction mixture was stirred at room temperature for 8 h, and treated with 132 μL (132 μmol) of 1 N HCl. The solution was extracted with CHCl$_3$ and the organic layer was dried (Na$_2$SO$_4$) and concentrated in vacuo to give the crude acid as a colorless form. This acid was dissolved in 2.00 mL of CHCl$_3$ and treated at room temperature with 2.1 mg (16 μmol) of HOBt, 3.0 mg (16 μmol) of EDC, 3.3 mg (20 μmol) of 2-amino-5,6-dihydro-6-methyl-4H-1,3-thiazine.HCl and 3.5 mg (27 μmol) of DMAP. The reaction mixture was stirred at room temperature for 48 h, diluted with CHCl$_3$, and washed with H$_2$O. The organic layer was dried (Na$_2$SO$_4$), concentrated in vacuo, and purified by chromatography on SiO$_2$ (1:1, hexanes/EtOAc followed by 20:1, CHCl$_3$/MeOH) to yield 11 mg (89%) of XJB-5-241 as a colorless powder. The following characterization data were obtained: LC-MS (R$_t$ 8.37 min, linear gradient 70% to 95% CH$_3$CN (H$_2$O) in 10 min, 0.4 mL/min; m/z=932.4 [M+H]$^+$, 954.3 [M+Na]$^+$) and HRMS (ESI) m/z calculated for C$_{50}$H$_{74}$N$_7$O$_8$S (M+H) 932.5320. found 932.5318.

Compound (2) is Boc-Leu-ψ[(E)-CH=CH]-ᴰPhe-Pro-Val-Orn(Cbz)-AMT (XJB-5-133) and was prepared according to the following protocol. A solution of 20.0 mg (24.3 µmol) of 2-85 (XJB-5-194) in 800 µL of MeOH was treated at 0° C. with 243 µL (243 µmol) of 1 N NaOH. The reaction mixture was stirred at room temperature for 6 h, and treated with 243 µL (243 µmol) of 1 N HCl. The solution was extracted with CHCl₃ and the organic layer was dried (Na₂SO₄) and concentrated in vacuo to give the crude acid as a colorless form. This acid was dissolved in 1.00 mL of CHCl₃ and treated at room temperature with 3.9 mg (29 µmol) of HOBt, 5.6 mg (29 µmol) of EDC, 6.1 mg (37 µmol) of 2-amino-5,6-dihydro-6-methyl-4H-1,3-thiazine.HCl and 7.4 mg (61 µmol) of DMAP. The reaction mixture was stirred at room temperature for 20 h, diluted with CHCl₃, and washed with H₂O. The organic layer was dried (Na₂SO₄), concentrated in vacuo, and purified by chromatography on SiO₂ (1:1, hexanes/EtOAc followed by 20:1, CHCl₃/MeOH) and an additional preparative C18 reverse phase HPLC purification was performed: 80% to 100% CH₃CN (H₂O) in 20 min, 5.0 mL/min) to afford 12.9 mg (58%) of XJB-5-133 as a colorless powder. The following characterization data were obtained: LC-MS($R_t$ 7.89 min, linear gradient 70% to 95% CH₃CN (H₂O) in 10 min, 0.4 mL/min; m/z=918.3 [M+H]⁺, 940.3 [M+Na]⁺) and HRMS (ESI) m/z calculated for $C_{49}H_{72}N_7O_8S$ (M+H) 918.5163. found 918.5185.

(3)

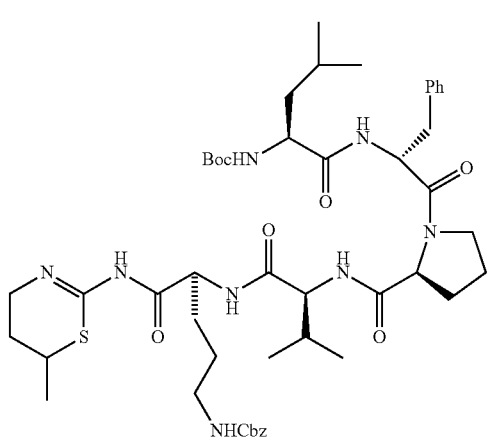

Compound (3) is Boc-Leu-ᴰPhe-Pro-Val-Orn(Cbz)-AMT (XJB-5-127). According to the following protocol. A solution of 24.0 mg (28.7 µmol) of Boc-Leu-ᴰPhe-Pro-Val-Orn(Cbz)-OMe in 800 µL of MeOH was treated at room temperature with 287 µL (287 µmol) of 1 N NaOH. The reaction mixture was stirred at room temperature for 5 h, and treated at 0° C. with 287 µL (287 µmol) of 1 N HCl. The solution was extracted with CHCl₃ and the organic layer was dried (Na₂SO₄) and concentrated in vacuo to give the crude acid as a colorless foam. The crude acid was dissolved in 2.00 mL of CHCl₃ and treated at room temperature with 4.6 mg (34 µmol) of HOBt, 6.6 mg (34 µmol) of EDC, 5.7 mg (34 µmol) of 2-amino-5,6-dihydro-6-methyl-4H-1,3-thiazine.HCl and 8.8 mg (72.0 µmol) of DMAP. The reaction mixture was stirred at room temperature for 24 h, diluted with CHCl₃, and washed with H₂O. The organic layer was dried (Na₂SO₄), concentrated in vacuo, and purified by chromatography on SiO₂ (2:1, hexanes/EtOAc followed by 20:1, CHCl₃/MeOH) to yield 17.0 mg (63%) of XJB-5-127 as a colorless powder. The following characterization data were obtained: LC-MS($R_t$ 6.32 min, linear gradient 70% to 95% CH₃CN (H₂O) in 10 min, 0.4 mL/min; m/z=935.3 [M+H]⁺, 957.3 [M+Na]⁺) and HRMS (ESI) m/z calculated for $C_{48}H_{71}N_8O_9S$ (M+H) 935.5065. found 935.5044.

(4)

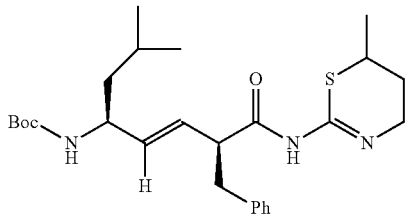

Compound (4) is Boc-Leu-ψ[(E)-CH=CH]-ᴰPhe-AMT (XJB-5-234). A solution of crude Boc-Leu-ψ[(E)-CH=CH]-ᴰPhe-OH (2-84) (30.5 µmol) in 2.00 mL of CH₂Cl₂ was treated at 0° C. with 6.1 mg (37 µmol) of 2-amino-5,6-dihydro-6-methyl-4H-1,3-thiazine.HCl, 7.0 mg (37 µmol) of EDC, 4.9 mg (37 µmol) of HOBt, and 9.3 mg (76 µmol) of DMAP. The reaction mixture was stirred at room temperature overnight, concentrated in vacuo, and purified by chromatography on SiO₂ (2:1, CH₂Cl₂/EtOAc) to yield 9.1 mg (63%) of XJB-5-234 as a colorless foam. The following characterization data were obtained: LC-MS($R_t$ 8.42 min, linear gradient 70% to 95% CH₃CN (H₂O) in 10 min, 0.4 mL/min; m/z=474.5 [M+H]⁺) and HRMS (ESI) m/z calculated for $C_{26}H_{40}N_3O_3S$ (M+H) 474.2790. found 474.2781.

(5)

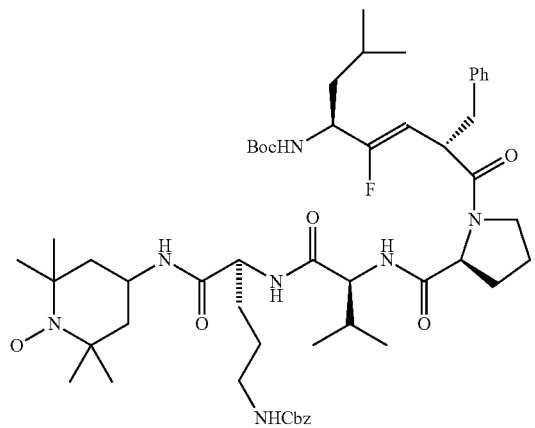

Compound (5) is Boc-Leu-ψ[(Z)—CF=CH]-ᴰPhe-Pro-Val-Orn(Cbz)-TEMPO (XJB-7-53). A solution of 3.4 mg (4.1 µmol) of Boc-Leu-ψ[(Z)—CF=CH]-ᴰPhe-Pro-Val-Orn(Cbz)-OMe XJB-5-66) in 400 µL of MeOH was treated at 0° C. with 41 µL (41 µmol) of 1 N NaOH. The reaction mixture was stirred at room temperature for 12 h, and treated with 41 µL (41 µmol) of 1 N HCl. The solution was extracted with CHCl₃ and the organic layer was dried (Na₂SO₄) and concentrated in vacuo to give the crude acid as a colorless form. This acid was dissolved in 400 µL of CHCl₃ and treated at room temperature with 0.7 mg (5 µmol) of HOBt, 0.9 mg (5 µmol) of EDC, 0.5 mg (4 µmol) of 4-amino-TEMPO and 1.1 mg (6 µmol) of DMAP. The reaction mixture was stirred at room temperature for 12 h, diluted with CHCl₃, and washed with H₂O. The organic layer was dried (Na₂SO₄), concentrated in vacuo, and purified by chromatography on SiO₂ (1:1, hexanes/EtOAc followed by 20:1, CHCl₃/MeOH) to yield 3.6 mg (91%) of XJB-7-53 as a colorless powder. The following characterization data were obtained: LC-MS(R$_t$ 8.45 min, linear gradient 70% to 95% CH₃CN (H₂O) in 10 min, 0.4 mL/min; m/z=977.5 [M+H]⁺, 999.5 [M+Na]⁺) and HRMS (ESI) m/z calculated for $C_{53}H_{79}FN_7O_9Na$ (M+Na) 999.5821.

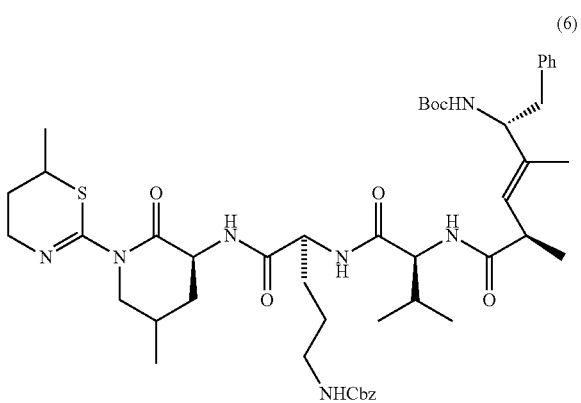

(6)

Compound (6) is Boc-$^D$Phe-ψ[(E)-C(CH₃)=CH]-Ala-Val-Orn(Cbz)-Leu-AMT (XJB-7-42) and was prepared according to the following protocol. A solution of 4.5 mg (5.6 μmol) of Boc-$^D$Phe-ψ[(E)-C(CH₃)=CH]-Ala-Val-Orn(Cbz)-Leu-OMe (2-119) in 0.35 mL of MeOH was treated at 0° C. with 56 μL (56 μmol) of 1 N NaOH. The reaction mixture was stirred at room temperature for 12 h, and treated with 56 μL (56 μmol) of 1 N HCl. The solution was extracted with CHCl₃ and the organic layer was dried (Na₂SO₄) and concentrated in vacuo to give the crude acid as a colorless form. This acid was dissolved in 0.80 mL of CHCl₃ and treated at room temperature with 0.9 mg (6.7 μmol) of HOBt, 1.3 mg (6.7 μmol) of EDC, 1.4 mg (8.4 μmol) of 2-amino-5,6-dihydro-6-methyl-4H-1,3-thiazine.HCl and 1.7 mg (14 μmol) of DMAP. The reaction mixture was stirred at room temperature for 36 h, concentrated in vacuo, and purified by chromatography on SiO₂ (20:1, CHCl₃/MeOH) to yield 5.0 mg (99%) of XJB-7-42 as a colorless foam. The following characterization data were obtained: LC-MS(R$_t$ 6.61 min, linear gradient 70% to 95% CH₃CN (H₂O) in 10 min, 0.4 mL/min; m/z=907.3 [M+H]⁺, 929.4 [M+Na]⁺) and HRMS (ESI) m/z calculated for $C_{48}H_{72}N_7O_8S$ (M+H) 906.5163. found 906.5190.

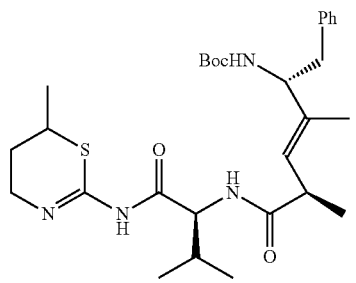

(7)

Compound (7) is Boc-$^D$Phe-ψ[(E)-C(CH₃)=CH]-Ala-Val-AMT (XJB-7-43). A solution of 14.3 μmol of crude Boc-$^D$Phe-ψ[(E)-C(CH₃)=CH]-Ala-Val-OMe (2-111) in 1.00 mL of CHCl₃ was treated at room temperature with 2.3 mg (17 μmol) of HOBt, 3.3 mg (17 μmol) of EDC, 3.6 mg (22 μmol) of 2-amino-5,6-dihydro-6-methyl-4H-1,3-thiazine.HCl and 4.4 mg (36 μmol) of DMAP. The reaction mixture was stirred at room temperature for 36 h, concentrated in vacuo, and purified by chromatography on SiO₂ (20:1, CHCl₃/MeOH) to yield 7.5 mg (96%) of XJB-7-43 as a colorless foam. The following characterization data were obtained: LC-MS(R$_t$ 5.41 min, linear gradient 70% to 95% CH₃CN (H₂O) in 10 min, 0.4 mL/min; m/z=545.3 [M+H]⁺, 567.3 [M+Na]⁺) and HRMS (ESI) m/z calculated for $C_{29}H_{44}N_4O_4S$ (M+Na) 567.2981. found 567.2971.

Among the preferred radical scavenging agents are a material selected from the group consisting of a ubiquinone analog, a ubiquinone analog fragment moiety, a ubiquinone analog fragment moiety lacking a hydrophilic tail, a superoxide dismutase mimetic, a superoxide dismutase biomimetic or a salen-manganese compound.

As is known to one ordinarily skilled in the art, ionizing radiation activates a mitochondrial nitric oxide synthase ("mtNOS"), leading to inhibition of the respiratory chain, generation of excess superoxide radicals, peroxynitrite production and nitrosative damage. The damage done by ionizing radiation is believed to be alleviated [See Kanai, A. J. et al., AMERICAN JOURNAL OF PHYSIOLOGY 383: F1304-F1312 (2002); and Kanai, A. J. et al., AMERICAN JOURNAL OF PHYSIOLOGY 286: H13-H21 (2004)]. The composition of this embodiment is characterized by the property of inhibiting mtNOS, thereby resisting generation of excess superoxide radicals, peroxynitrite and nitrosative damage.

Protection again irradiation damage using systemic drug delivery can result in unwanted side effects. One approach to limit or prevent these adverse side affects is to target drug delivery to the mitochondria using a peptide carrier strategy.

The present invention may employ a Gramicidin-S fragment moiety that can be varied in length and the Orn side chain amines can be acylated to modulate passage through the cell membrane and mitochondrial targeting.

In a preferred embodiment of the invention, a potent NOS inhibitor, the non-arginine analog of 2-amino-6-methyl-thiazine ("AMT"), was selected. Irradiation of the ureopithelium results in increased production of superoxide and nitric oxide ("NO"), mouse bladders were instilled with AMT or 4-amino-TEMPO to determine if inhibition of NO or scavenging free radicals is more radioprotective.

An unconjugated and conjugated NOS antagonist, (AMT, 100 μM) and an unconjugated and conjugated nitroxide derivative (4-amino-TEMPO, 100 μM) were incubated for two hours at 37° C. with 32D c13 hemopoietic cells.

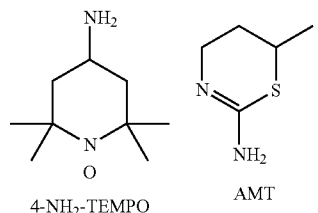

4-NH₂-TEMPO          AMT

Following incubation, the cells were lysed and the mitochondria isolated for a mass spectrometry analysis where compounds isolated from mitochondria were identified as Na+ adducts. The resulting spectra (not shown) demonstrate that 4-amino-TEMPO only permeate the mitochondrial membrane with the assistance of the attached GS-derived targeting sequence. Further spectra (not shown) indicate that unconjugated AMT do not enter the mitochondria membrane in substantial quantities. Thus, the targeting peptides successfully direct a NOS antagonist and a nitroxide to the mitochondria.

Further physiological studies were conducted to determine the effects of peptide-targeted AMT and 4-amino-TEMPO on NO and peroxynitrite production in irradiated uroepithelial cells. The cells were cultured in an 8-well slide chamber for 3 days and then microsensor measurements were taken 24 hours after irradiation.

In untreated irradiated cells and cells treated with unconjugated 4-amino-TEMPO (100 µM) or unconjugated AMT (10 µM), capsaicin evoked NO production and resulted in the formation of comparable amount of peroxynitrite. In cells treated with high-dose conjugated 4-amin-TEMPO (100 µM), peroxynitrite production was decreased by approximately 4-fold. In non-radiated cells or cells treated with conjugated AMT (10 µM), NO induced peroxynitrite formation was nearly completely inhibited. This suggested that peptides conjugates couple or covalently link with membrane impermeant 4-amino-TEMPO or AMT and facilitate the transport of 4-amin-TEMPO across the mitochondrial membrane. Furthermore, this data suggests that the peptide conjugates do not interfere with the NOS inhibitory activity of AMT or the free radical scavenging activity of 4-amino-TEMPO and that AMT is a more effective radioprotectant [Kanai, A. J. et al., Mitochondrial Targeting of Radioprotectants Using Peptidyl Conjugates, ORGANIC AND BIOMOLECULAR CHEMISTRY (in press)].

Quantitative mass spectrometry studies were used to compare the effectiveness of several AMT peptide conjugates in permeating the mitochondrial membrane, specifically XJB-5-234, XJB-5-133, XJB-5-241, and XJB-5-127. The Fmole/10 µM mitochondrial protein ratio provides a relative quantification of conjugate concentration at the target site. Table 2 indicates that the most efficacious conjugate was compound XJB-5-241.

TABLE 2

| Compound | Fmole/10M mitochondrial protein |
|---|---|
| XJB-5-234 | 1.45 |
| XJB-5-133 | 89.8 |
| XJB-5-241 | 103.3 |

The trisubstituted (E)-alkene moiety embedded in XJB-5-241 has a stronger conformational effect that the less biologically active disubstituted (E)-alkene XJB-5-133 or the GS peptidyl fragment XJB-5-127, see Wipf P. et al., *Methyl-and (Triluoromethyl)alkene Peptide Isosteres: Synthesis and Evaluation of Their Potential as β-Turn Promoters and Peptide Mimetics* J ORG. CHEM. 63:6088-6089 (1998); also Wipf P. et al., *Imine Additions of Internal Alkynes for the Synthesis of Trisubstituted (E)-Alkene and Cyclopropane Peptide Isosteres* ADV. SYNTH. CAT. 347:1605-1613 (2005). The data indicates that a defined secondary structure and an appropriate conformational preorganization is important in accomplishing mitochondrial permeation of compounds that reduce nitrosative and oxidative effects.

The presence of a non-hydrolyzable alkene isostere functions in place of labile peptide bonds and is significant for a prolonged mechanism of action. The relatively rigid (E)-alkenes ($\psi$[(E)-C(R)=CH]) represent useful, conformationally preorganized structural mimetics and have been used as surrogates of hydrolytically labile amide bonds in a number of enzyme inhibitors. The primary objective of this strategy is the accurate mimicry of the geometry of the peptide bond; however, (E)-alkenes also modulate the physicochemical properties, solubility, and lipophilicity, number of hydrogen donors and acceptors, etc, of the parent structures, and therefore generally have a different metabolic fate than simple peptides.

A targeted delivery strategy employed in this invention is advantageous since some neuronal NOS (nNOS) antagonists and most antioxidants, including nitroxide derivatives, are poorly cell-permeable and require therapeutically effective concentrations greater than 100 µM if used without a conjugate.

The method related to this embodiment of the invention delivers a composition to mitochondria comprising transporting to said mitochondria a desired cargo which may, for example, be (a) a radical scavenging agent by use of a membrane active peptidyl fragment preferably having has a β-turn motif having a high affinity for the mitochondrial membrane or (b) a nitric oxide synthase antagonist bonded to the membrane active peptidyl fragment.

Whereas particular embodiments of this invention have been described above for purposes of illustration, it will be evident to those skilled in the art that numerous variations of the details of the present invention may be made without departing from the invention as defined in the appended claims.

What is claimed is:

1. A method of delivering a cargo to a mitochondria of a patient comprising administering to a patient a mitochondria-targeting compound comprising a membrane-active fragment of gramicidin S or an E-alkylene isostere thereof conjugated to a cargo, wherein the fragment of gramicidin S or E-alkylene isostere thereof has the sequence of one of:

Leu-$^D$Phe-Pro-Val-Orn; or

Leu-(E)-$^D$Phe-Pro-Val-Orn.

2. The method of claim 1, in which the gramicidin S fragment or E-alkylene isostere thereof comprises a β-turn.

3. The method of claim 1, in which an amine of the gramicidin S fragment or E-alkylene isostere thereof is acylated.

4. The method of claim 1, in which an amine of the gramicidin S fragment or E-alkylene isostere thereof is acylated with Boc and/or Cbz.

5. The method of claim 1, in which the cargo is a reactive-oxygen species (ROS) scavenger or an NOS inhibitor.

6. The method of claim 5, in which the cargo is a nitroxide reactive-oxygen species (ROS) scavenger.

7. The method of claim 1, in which the in which the cargo is TEMPO or 4-amino TEMPO.

8. The method of claim 1, in which the cargo is conjugated to the compound of formula A:

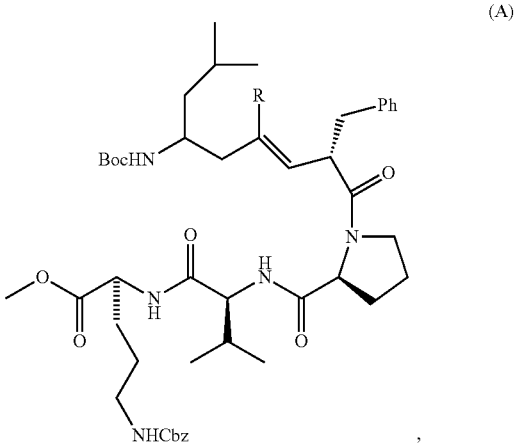

(A)

where R is H or methyl.

9. The method of claim 8, in which the cargo is TEMPO or 4-amino TEMPO, and in which the compound is administered to treat a patient for a condition associated with or caused by reactive oxygen species (ROS).

10. A method of delivering a cargo to a mitochondria of a patient comprising administering to a patient a mitochondria-targeting compound comprising a cargo conjugated to the compound of Formula B:

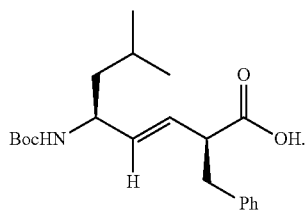

(B)

11. The method of claim 1, in which the compound is XJB-5-131.

12. The method of claim 1, in which the compound is administered to treat a patient for a condition associated with or caused by reactive oxygen species (ROS), and the cargo is an ROS scavenger.

13. The method of claim 12, in which the condition is hemorrhagic shock.

14. A compound comprising a membrane-active fragment of gramicidin S or an E-alkylene isostere thereof conjugated to a cargo, wherein the fragment of gramicidin S or E-alkylene isostere thereof has the sequence of one of:

Leu-$^D$Phe-Pro-Val-Orn; or

Leu-(E)-$^D$Phe-Pro-Val-Orn.

15. The compound of claim 14, in which the gramicidin S fragment or E-alkylene isostere thereof comprises a β-turn.

16. The compound of claim 14, in which the gramicidin S fragment or E-alkylene isostere thereof has the sequence Leu-$^D$Phe-Pro-Val-Orn.

* * * * *